US012110355B2

(12) United States Patent
Hamachi et al.

(10) Patent No.: US 12,110,355 B2
(45) Date of Patent: *Oct. 8, 2024

(54) METHOD FOR PRODUCING CONJUGATED DIENE POLYMER

(71) Applicant: SEKISUI CHEMICAL CO., LTD., Osaka (JP)

(72) Inventors: Kokoro Hamachi, Tsukuba (JP); Noritoshi Yagihashi, Tsukuba (JP); Haruka Nishiyama, Tsukuba (JP); Kazuto Natsuyama, Tsukuba (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 441 days.

This patent is subject to a terminal disclaimer.

(21) Appl. No.: 17/297,770

(22) PCT Filed: Jan. 28, 2020

(86) PCT No.: PCT/JP2020/003031
§ 371 (c)(1),
(2) Date: May 27, 2021

(87) PCT Pub. No.: WO2020/158751
PCT Pub. Date: Aug. 6, 2020

(65) Prior Publication Data
US 2021/0395421 A1   Dec. 23, 2021

(30) Foreign Application Priority Data

| Jan. 28, 2019 | (JP) | 2019-012564 |
| Jan. 28, 2019 | (JP) | 2019-012568 |
| Mar. 18, 2019 | (JP) | 2019-050436 |
| Mar. 18, 2019 | (JP) | 2019-050465 |
| Mar. 18, 2019 | (JP) | 2019-050472 |
| Mar. 18, 2019 | (JP) | 2019-050474 |
| Mar. 18, 2019 | (JP) | 2019-050480 |
| Mar. 18, 2019 | (JP) | 2019-050484 |
| Mar. 18, 2019 | (JP) | 2019-050489 |
| Jun. 25, 2019 | (JP) | 2019-117720 |
| Jun. 25, 2019 | (JP) | 2019-117745 |
| Jun. 25, 2019 | (JP) | 2019-117749 |
| Jun. 25, 2019 | (JP) | 2019-117754 |
| Jul. 5, 2019  | (JP) | 2019-126455 |

(51) Int. Cl.

| C08F 36/04  | (2006.01) |
| C07C 1/24   | (2006.01) |
| C07C 29/80  | (2006.01) |
| C07C 31/08  | (2006.01) |
| C07C 67/08  | (2006.01) |
| C08C 19/00  | (2006.01) |
| C08F 236/10 | (2006.01) |
| C08J 3/20   | (2006.01) |
| C10J 3/72   | (2006.01) |
| C10K 1/00   | (2006.01) |
| C10L 1/02   | (2006.01) |
| C12N 1/20   | (2006.01) |

(Continued)

(52) U.S. Cl.
CPC .............. C08F 236/10 (2013.01); C07C 1/24 (2013.01); C07C 29/80 (2013.01); C07C 31/08 (2013.01); C07C 67/08 (2013.01); C08C 19/00 (2013.01); C08J 3/203 (2013.01); C10J 3/72 (2013.01); C10K 1/005 (2013.01); C10L 1/02 (2013.01); C12N 1/20 (2013.01); C12P 7/06 (2013.01); C12P 7/065 (2013.01); C12P 7/08 (2013.01); B60C 1/0016 (2013.01); B60C 1/0025 (2013.01); B60C 1/0041 (2013.01); B60C 2001/005 (2013.01); C08F 36/06 (2013.01); C08F 36/08 (2013.01); C08J 2309/06 (2013.01); C10J 2300/0946 (2013.01); C10J 2300/1665 (2013.01); C10L 2290/26 (2013.01); C12R 2001/145 (2021.05)

(58) Field of Classification Search
None
See application file for complete search history.

(56) References Cited

U.S. PATENT DOCUMENTS

| 5,258,293 A | * | 11/1993 | Lynd | ........................ C12P 7/14 435/813 |
| 6,136,577 A | | 10/2000 | Gaddy | |

(Continued)

FOREIGN PATENT DOCUMENTS

| CN | 107001177 A  | 8/2017 |
| EP | 2 543 654 A1 | 1/2013 |

(Continued)

OTHER PUBLICATIONS

De Baerdemaeker, T. et al., "Bimetallic Zn and Hf on Silica Catalysts for the Conversion of Ethanol to 1,3-Butadiene". ACS Catalysis 2015, 5(6), 3393-3397. (Year: 2015).*

(Continued)

*Primary Examiner* — Richard A Huhn
(74) *Attorney, Agent, or Firm* — Sughrue Mion, PLLC

(57) ABSTRACT

[Problem to be Solved] Provided is a method for producing a non-petrochemical-derived conjugated diene polymer using an alcohol derived from a non-petrochemical raw material.

[Means to Solve the Problem] In the present invention, the method is characterized in that a non-petrochemical-derived conjugated diene polymer is produced using an alcohol derived from a non-petrochemical raw material having an iron content of 0.0001 mg/L to 2 mg/L.

10 Claims, No Drawings

(51) Int. Cl.
| | |
|---|---|
| *C12P 7/06* | (2006.01) |
| *C12P 7/08* | (2006.01) |
| *B60C 1/00* | (2006.01) |
| *C08F 36/06* | (2006.01) |
| *C08F 36/08* | (2006.01) |
| *C12R 1/145* | (2006.01) |

(56) References Cited

U.S. PATENT DOCUMENTS

| | | |
|---|---|---|
| 2004/0181101 A1 | 9/2004 | Fanselow et al. |
| 2011/0136962 A1* | 6/2011 | Hattori .................. C08K 3/36 524/493 |
| 2012/0052541 A1 | 3/2012 | Oakley |
| 2017/0260552 A1 | 9/2017 | Haas et al. |
| 2018/0002249 A1 | 1/2018 | Vecchini et al. |

FOREIGN PATENT DOCUMENTS

| | | |
|---|---|---|
| EP | 2 868 697 A1 | 5/2015 |
| EP | 2 883 909 A1 | 6/2015 |
| EP | 3 246 301 A1 | 11/2017 |
| JP | 2007-246712 A | 9/2007 |
| JP | 2011-512869 A | 4/2011 |
| JP | 2011-514236 A | 5/2011 |
| JP | 2012-97163 A | 5/2012 |
| JP | 2012-122016 A | 6/2012 |
| JP | 2012-518658 A | 8/2012 |
| JP | 2012-205530 A | 10/2012 |
| JP | 2013-49023 A | 3/2013 |
| JP | 2013-515482 A | 5/2013 |
| JP | 2014-074121 A | 4/2014 |
| JP | 2014-105323 A | 6/2014 |
| JP | 2014-518089 A | 7/2014 |
| JP | 2014-148683 A | 8/2014 |
| JP | 2015-42711 A | 3/2015 |
| JP | 2016-059296 A | 4/2016 |
| JP | 2016-524927 A | 8/2016 |
| JP | 2017-2168 A | 1/2017 |
| JP | 2018-058042 A | 4/2018 |
| JP | 2018-510848 A | 4/2018 |
| JP | 2018-70465 A | 5/2018 |
| JP | 2019-88240 A | 6/2019 |
| WO | 2009/112334 A1 | 9/2009 |
| WO | 2012/102290 A1 | 8/2012 |
| WO | 2014/038647 A1 | 3/2014 |
| WO | 2015/037710 A1 | 3/2015 |
| WO | 2015/058011 A1 | 4/2015 |
| WO | 2017/221987 A1 | 12/2017 |

OTHER PUBLICATIONS

Sekisui Chemical Co., Ltd. Supplemental reply made on Jan. 27, 2022 in European Patent Application No. 20749153.1. (Year: 2022 ).*
Communication, dated Aug. 13, 2021, issued by the European Patent Office in European Patent Application No. 20 749 153.1.
Notification of Reasons for Refusal dated Apr. 11, 2023 from the Japan Patent Office in application No. 2019-117720.
Notification of Reasons for Refusal dated Apr. 11, 2023 from the Japan Patent Office in application No. 2019-117745.
Notification of Reasons for Refusal dated Apr. 11, 2023 from the Japan Patent Office in application No. 2019-117749.
Notification of Reasons for Refusal dated Apr. 11, 2023 from the Japan Patent Office in application No. 2019-117754.
Office Action issued Jan. 6, 2023 in Japanese Application No. 2019-050472.
Office Action issued Jan. 6, 2023 in Japanese Application No. 2019-012564.
Office Action issued Jan. 6, 2023 in Japanese Application No. 2019-050474.
Office Action issued Jan. 6, 2023 in Japanese Application No. 2019-050480.
Office Action issued Jan. 6, 2023 in Japanese Application No. 2019-050484.
Office Action issued Jan. 6, 2023 in Japanese Application No. 2019-050489.
International Search Report for PCT/JP2020/003031 dated Apr. 14, 2020 [PCT/ISA/210].
Communication, dated Aug. 12, 2021, issued by the International Bureau in International Application No. PCT/JP2020/003031.
Japanese Office Action issued Sep. 5, 2023 in Application No. 2020-016613.
Carlos Sanchez et at., "Metal and metalloid determination in bioethanol through inductively coupled plasma-optical emission spectroscopy", Spectrochimica Acta. Part B, 2016, vol. 115, pp. 16-22 (7 pages total).
"Margarita mix", Brand: NINA'S, Aug. 9, 2018, Food Data Central (4 pages total).
United States Office Action issued Sep. 27, 2023 in U.S. Appl. No. 17/422,654.
Chinese Office Action issued Jul. 7, 2023 in Application No. 202080011053.7.
Tatiana Dillenburg Saint'Pierre et al., "The development of a method for the determination of trace elements in fuel alcohol by electrothermal vaporization-inductively coupled plasma mass spectrometry using external calibration*," Spectrochimica Acta Part B, vol. 60, pp. 605-613 (9 pages total).
Office Action issued Oct. 6, 2023 in Japanese Application No. 2019-117745.
Office Action issued Oct. 10, 2023 in Japanese Application No. 2019-117720.
Office Action issued Oct. 10, 2023 in Japanese Application No. 2019-117749.
Office Action issued Oct. 10, 2023 in Japanese Application No. 2019-117754.
European Search Report, dated Jul. 5, 2021, issued by the European Patent Office in European Application No. 20749153.1.
Jamal Abrini et al., "Clostridium autoethanogenum, sp. nov., an anaerobic bacterium that produces ethanol from carbon monoxide", Archives of Microbiology, 1994, vol. 161, No. 4, pp. 345-351 (7 pages total).
Japanese Office Action dated Feb. 14, 2023 in Japanese Application No. 2019-050436.
European Office Action dated Feb. 17, 2023 in European Application No. 20749002.0.
Office Action issued Nov. 29, 2023 in Chinese Application No. 202080011240.5.
Communication dated Apr. 19, 2024 issued by the Japanese Patent Office in application No. 2019- 117720.
Communication dated Apr. 19, 2024 issued by the Japanese Patent Office in application No. 2019- 117749.
Communication dated Apr. 19, 2024 issued by the Japanese Patent Office in application No. 2019-117754.
Communication dated May 7, 2024 issued by the Japanese Patent Office in application No. 2019-117745.
Communication dated Apr. 23, 2024 issued by the Japanese Patent Office in application No. 2019- 117745.
Communication dated Apr. 4, 2024 issued by the United States Patent and Trademark Office in U.S. Appl. No. 17/422,654.
Fredrik Aldaeus, et al., "Prediction of retention times of polycyclic aromatic hydrocarbons and *n*-alkanes in temperature-programmed gas chromatography", Anal Bioanal Chem, 2007, vol. 389, pp. 941-950.
The Interstate Technology & Regulatory Council (ITRC) Petroleum Vapor Intrusion Team, "Appendix C" of "Petroleum Vapor Intrusion: Fundamentals of Screening, Investigation, and Management", Oct. 2014, pp. 129-134 (9 pages total).
Fabio Monticelli, et al., "Another case of diethyl ether intoxication? A case report focusing on toxicological analysis", Legal Medicine, vol. 13, 2011, pp. 254-258.
Jana Šťávová, et al., "Method development for the characterization of biofuel intermediate products using gas chromatography with

(56) References Cited

OTHER PUBLICATIONS simultaneous mass spectrometric and flame ionization detections", Journal of Chromatography A, vol. 1224, 2012, pp. 79-88.

"Alkyl", Wikipedia, Archived via The Wayback Machine, Mar. 25, 2017, pp. 1-4, https://web.archive.org/web/20170325081756/https://en.wikipedia.org/wiki/Alkyl_group.

United States Office Action dated Jun. 21, 2024 in U.S. Appl. No. 18/387,137.

Notice of Reasons for Refusal dated Jun. 21, 2024 in Japanese Application No. 2023-121066.

Notice of Reasons for Refusal dated Jun. 21, 2024 in Japanese Application No. 2023-121071.

Notice of Reasons for Refusal dated Jun. 21, 2024 in Application No. 2023-121080.

Chinese Office Action dated Jul. 9, 2024 in Chinese Application No. 202080011240.5.

Notice of Reasons for Refusal dated Jul. 12, 2024 in Japanese Application No. 2023-133155.

Notice of Reasons for Refusal dated Jul. 12, 2024 in Japanese Application No. 2023-133156.

Notice of Reasons for Refusal dated Jul. 12, 2024 in Japanese Application No. 2023-133158.

Notice of Reasons for Refusal dated Jul. 12, 2024 in Japanese Application No. 2023-133159.

Decision of Refusal dated Jul. 30, 2024 in Japanese Application No. 2020-016613.

\* cited by examiner

METHOD FOR PRODUCING CONJUGATED DIENE POLYMER

CROSS-REFERENCE TO RELATED APPLICATIONS

This application is a National Stage of International Application No. PCT/JP2020/003031, filed Jan. 28, 2020, claiming priority based on Japanese Patent Application Nos. 2019-012564 and 2019-012568 filed on Jan. 28, 2019; Japanese Patent Application Nos. 2019-050436, 2019-050465, 2019-050472, 2019-050474, 2019-050480, 2019-050484, and 2019-050489 filed on Mar. 18, 2019; Japanese Patent Application Nos. 2019-117720, 2019-117745, 2019-117749 and 2019-117754 filed on Jun. 25, 2019; and Japanese Patent Application No. 2019-126455 filed on Jul. 5, 2019; the entire contents of which are incorporated herein by reference.

BACKGROUND OF THE INVENTION

Field of the Invention

The present invention relates to a method for producing a conjugated diene polymer. More specifically, the present invention relates to a method for producing a conjugated diene polymer derived from a non-petrochemical raw material using, as a raw material, an alcohol derived from a non-petrochemical raw material such as ethanol in which the content of a specific minor component is adjusted.

BACKGROUND ART

Petrochemical products are used in various places in our lives. On the other hand, owing to the popularity of the products, mass production and mass consumption have caused various environmental problems, resulting in major problems on a global scale. For example, typical petrochemical products as polyethylene and polyvinyl chloride are consumed in large quantities and disposed of, and these wastes have become a major cause of environmental pollution. Additionally in the context of mass production of petrochemical products, discussions are made on global environmental issues such as concerns on the depletion of fossil fuel resources and the increase in carbon dioxide in the atmosphere.

In view of the growing global awareness to such environmental problems, a method for producing various organic substances from raw materials other than naphtha, which is a raw material for petrochemical products, has recently been studied. For example, a method for producing bioethanol from an edible raw material such as corn by a sugar fermentation method is drawing attention. However, it has been pointed out that the sugar fermentation method using such edible raw materials has a problem of bringing about price escalation of food, for example, since the limited farmland area will be used for the production of other than food.

In order to solve this problem, there have been studies to use non-edible raw materials which have been conventionally disposed of. Specifically, there are proposed a method for producing alcohols by a fermentation method using cellulose derived from waste material or waste paper as a non-edible raw material, a method for gasifying biomass raw material as above and producing alcohols from synthetic gases using catalysts, and the like; however, none have not yet been put into practical use. Even if a variety of petrochemical products can be manufactured from these depetrochemical materials, since they will eventually become waste plastics that do not decompose naturally, they are not found effective as fundamental solutions for environmental problems.

At present, the amount of combustible waste disposed of in Japan reaches about 60 million tons/year. The amount of energy is equivalent to about 200 trillion kilocalories, which is much larger than the amount of energy contained in naphtha used as a raw material for plastics in Japan, and it can be said that these wastes are also heavy resources. If these waste resources can be converted into petrochemical products, it will be possible to realize an ultimate resource recycling society independent of oil resources. From the above viewpoint, Patent Documents 1 and 2, etc. disclose a technique of producing synthetic gases (a gas containing CO and $H_2$ as the main components) from waste and producing ethanol from the synthetic gas by a fermentation method.

However, as pointed out in Patent Document 3, a synthetic gas produced from waste contains various impurities which have not been clarified, and since some are toxic to microorganisms, the productivity was a major problem in producing alcohols from the synthetic gas by microbial fermentation. Alcohols obtained by microbial fermentation of the synthetic gas also contain various components caused by impurities in the synthetic gas, and these components cannot be completely removed even by purification treatment such as distillation. Therefore, development of derivatives from alcohols obtained by microbial fermentation of synthetic gases has been a major technical problem.

Conventionally, synthetic rubber such as butadiene rubber (BR) and styrene-butadiene rubber (SBR), and fillers such as carbon black have been used as rubber compositions for tires; however these are highly dependent on raw materials derived from petroleum resources. In recent years, environmental issues became more important, and regulations on $CO_2$ emissions have become stricter. In addition, since the amount of petroleum existing is limited and the use of raw materials derived from petroleum resources is limited, it is required to develop a rubber composition for tires in which one part or all of the raw materials derived from petroleum resources currently used are replaced with raw materials derived from foreign petroleum sources. Patent Document 4 proposes increasing the ratio of natural rubber as the rubber component. Patent Document 5 proposes the use of modified natural rubber as the rubber component. Furthermore, Patent Document 6 proposes the use of renewable (bioresource-derived) butadiene or isoprene as butadiene or isoprene that is the raw material for the rubber component. Patent documents 7 and 8 propose the synthesis of 1,3-butadiene from commercially available bioethanol.

PRIOR ART DOCUMENTS

[Patent Document]
Patent Document 1: Japanese Patent Application Laid-Open Publication No. 2016-059296
Patent Document 2: WO2015/037710
Patent Document 3: Japanese Patent Application Laid-Open Publication No. 2018-058042
Patent Document 4: Japanese Patent Application Laid-Open Publication No. 2007-246712
Patent Document 5: Japanese Patent Application Laid-Open Publication No. 2012-122016
Patent Document 6: Japanese Patent Application Laid-Open Publication No. 2012-518658
Patent Document 7: WO2012/102290

Patent Document 8: Japanese Patent Application Laid-Open Publication No. 2014-148683

SUMMARY OF THE INVENTION

Problem to be Solved by the Invention

According to the study by the present inventors, the C2 raw material, for example, represented by conventional ethanol is known as a starting material for various chemical products; however as described above, it has been found that alcohols produced from resources independent of petroleum resources or biomass resources (circulation type resources) are different from the chemical raw material derived from naphtha and contain various trace amounts of unknown substances. Since the characteristics of the materials are unknown in the prior art, there has been no sufficient examination on whether all the materials should be removed or only the specific materials. Therefore, the current status is that even if alcohols produced from a recyclable resource were proposed in the above-mentioned patent document, there is still room for technical improvement in order to put the alcohols into practical use.

On the other hand, although the above-mentioned documents disclose general fermentation and distillation methods and optimum composition of the synthetic gas, the details of the process are not disclosed, neither has the alcohol substance obtained been identified.

The present invention has been made in consideration of such background art, and the object is to provide a practical and novel alcohol having industrial value more than the existing petrochemical raw materials and a derivative thereof.

In addition, Patent Document 6 discloses a method for producing renewable butadiene, wherein an alcohol obtained by fermenting a biomass-derived saccharide is used as a starting material. In addition, Patent Documents 7 and 8 suggest synthesizing 1,3-butadiene from commercially available bioethanol. However, the commercially available alcohols or equivalent products (described in the comparative example) described in such known documents are not manufactured specifically for the purpose of a practical chemical product, and it was necessary to develop a raw material alcohol that can withstand the physical properties and characteristics of various practical products (for example, a resin and a product using the resin). Therefore, a wider technology has been required for the optimization of the application range of alcohols.

Means for Solving the Problem

The present inventors have conducted intensive studies to solve the above-mentioned problem, and as a result, it has been found that a variety of trace substances contained in an alcohol produced from a recyclable resource can be specified, and further the content can be controlled to a specific range by a novel production method, and additionally that various derivatives thereof exhibit superior effects compared with the existing alcohols. For example, in the step of synthesizing butadiene from ethanol, it has been found that the selectivity of butadiene was improved compared with the case of using the conventional ethanol, and a chemical product derived from an alcohol at a level equivalent to or higher than that of the existing alcohol or a product using the same can be obtained, and thus the present invention has been achieved.

More specifically, in the case of producing ethanol from a gas substrate using waste as a carbon source, containing carbon monoxide and hydrogen, it was found that the conversion of ethanol was improved when butadiene was synthesized from the ethanol, and upon detailed examination of the reason, it was found that the content of a specific metallic element was extremely low in the ethanol derived from a circulating resource using the gas containing carbon monoxide and hydrogen as a substrate. The present invention is based on such finding.

Further, as a result of intensive studies by the present inventors to solve the above-mentioned problem, it has been found that by producing a conjugated diene polymer such as butadiene using an alcohol such as ethanol derived from the above-described non-petrochemical raw material having an iron content within a specific range as a starting material, and conducting polymerization of the polymer to produce a conjugated diene polymer derived from a non-petrochemical raw material, a polymer suitable as a rubber composition for tires can be obtained. The present invention is also based on such finding.

That is, the present invention includes the following key points.

[1] A method for producing a non-petrochemical-derived conjugated diene polymer using an alcohol derived from a non-petrochemical raw material, comprising the steps of: using an alcohol derived from a non-petrochemical raw material having an iron content of 0.0001 mg/L to 2 mg/L, bringing the alcohol into contact with a catalyst and carrying out heating to produce a conjugated diene having $C_4$ to $C_{12}$ carbons; and polymerizing the monomer containing the conjugated diene to produce a non-petrochemical derived conjugated diene polymer.

[2] The method according to [1], wherein the alcohol derived from a non-petrochemical raw material comprises ethanol.

[3] The method according to [1] or [2], wherein the conjugated diene comprises at least one selected from the group consisting of 1,3-butadiene, isoprene, 1,3-pentadiene, 2,3-dimethyl-1,3-butadiene, 2-methyl-1,3-pentadiene, 1,3-hexadiene, 4,5-diethyl-1,3-octadiene, and 3-butyl-1,3-octadiene.

[4] The method according to any one of [1] to [3], wherein the alcohol derived from a non-petrochemical raw material uses a gas containing carbon monoxide and hydrogen as a substrate.

[5] The method according to any one of [1] to [4], wherein the alcohol derived from a non-petrochemical raw material is derived from microbial fermentation.

[6] The method according to [4], wherein the gas comprising carbon monoxide and hydrogen is derived from waste.

[7] The method according to any one of [1] to [6], wherein an aromatic hydrocarbon is further polymerized as a monomer.

[8] The method according to [7], wherein the aromatic hydrocarbon is at least one selected from the group consisting of styrene, methylstyrene, ethylstyrene, t-butylstyrene, α-methylstyrene, α-methyl-p-methylstyrene, chlorostyrene, bromostyrene, methoxystyrene, dimethylaminomethylstyrene, dimethylaminoethylstyrene, diethylaminomethylstyrene, diethylaminoethylstyrene, cyanoethylstyrene, and vinylnaphthalene.

[9] The method according to any one of [1] to [8], wherein the conjugated diene polymer includes at least one selected from the group consisting of isoprene rubber, butadiene rubber, styrene butadiene rubber, chloroprene rubber, and acrylonitrile butadiene rubber.

[10] A method for producing a cross-linked rubber, comprising the step of kneading the non-petrochemical-derived conjugated diene polymer obtained as a rubber component by the method described in any one of [1] to [9] with a filler, and carrying out cross-linking.

[11] A method for producing a tire using the cross-linked rubber obtained by the method described in [10].

According to the present invention, by using an alcohol, preferably ethanol, having a very low content of a specific metal element various different effects can be obtained as compared with the commercially available industrial alcohol. For example, according to the present invention, it is possible to improve the butadiene selectivity in the synthesis of butadiene using the ethanol as a raw material, it is also possible to improve the yield in the synthesis of SBR, to control the glass transition temperature of SBR, and to control the butadiene/styrene ratio. In addition, even with the existing alcohol, it is expected that the same effect can be obtained by adjusting the content of the specific metal element to an extremely low content.

The alcohol, preferably ethanol, used in the present invention can also be used as a raw material for the production of, for example, butadiene, ethylene, propylene, isobutene, acetaldehyde, acetic acid, ethyl acetate, methyl (meth)acrylate, ethyl-t-butyl ether ethylene glycol, ester compositions, polyester, acrylic acid, aminohexanoic acid, diethyl carbonate, polyethylene (PE), polyethylene terephthalate (PET), polypropylene (PP), polyisobutylene, polymethylmethacrylate (PMMA), ethylene propylene diene rubber (EPDM), polybutylene terephthalate (PBT), polyethylene furanoate (PEF), polyurethane (PU), and the like. The alcohol used in the present invention can be used in various applications in chemical products such as cosmetics, perfumes, fuels, antifreeze solutions, sanitizing agents, disinfectants, cleaning agents, fungi removers, detergents, hair shampoos, soaps, antiperspirants, face washing sheets, solvents, paints, adhesives, diluents, food additives, and the like.

Embodiment of the Invention

Hereinafter, one example of a preferred embodiment of the present invention will be described. However, the following embodiments are examples for illustrating the present invention, and the present invention shall not be limited in any way to the following embodiments.

Definition

In the present invention, "alcohol" refers to a compound in which the hydrogen atom of a hydrocarbon is replaced with a hydroxyl group (—OH). Specifically, examples of the lower alcohol include methanol (methyl alcohol), ethanol (ethyl alcohol), 2-propanol, ethylene glycol, glycerin, phenol, and the like, and ethanol is preferable. The higher alcohol is usually one having 8 to 22 carbon atoms, and specific examples thereof include capryl alcohol, lauryl alcohol, myristyl alcohol, cetyl alcohol (cetanol), stearyl alcohol, oleyl alcohol, and linoleyl alcohol.

In the present invention, the term "ethanol" does not mean pure ethanol as a compound (ethanol represented by chemical formula: $CH_3CH_2OH$), but means a composition containing water and impurities (contaminant components) inevitably contained in the ethanol produced through synthesis or purification.

In the present invention, the content of each component such as an inorganic component and an organic component in the alcohol raw material is the amount (mg) of each component with respect to 1 L of alcohol.

<Alcohol Derived from Non-Petrochemical Raw Materials>

In the present invention, use is made to an alcohol derived from a non-petrochemical raw material in which the content of Fe (iron) is controlled. Specifically, the content of Fe (iron) with respect to the alcohol is 0.0001 mg/L or more and 2 mg/L or less, preferably 0.0005 mg/L or more, more preferably 0.001 mg/L or more, still more preferably 0.01 mg/L or more, and preferably 1.5 mg/L or less, more preferably 1.0 mg/L or less, and still more preferably 0.5 mg/L or less.

The content of Fe is the amount in Fe element conversion of the Fe compound. When the content of Fe is in the above numerical range, the selectivity of butadiene in the synthesis of butadiene using ethanol as a raw material can be improved, the yield in the synthesis of SBR can be improved, and the glass transition temperature of SBR and the butadiene/styrene ratio can be controlled.

The content of iron in the alcohol can be measured by known methods. As a method for measuring the content of iron, for example, a method using an inductively coupled plasma mass spectrometry (ICP-MS) can be mentioned. In the analytical method using ICP-MS, a standard solution for atomic absorption is analyzed after concentration adjustment to prepare a calibration curve, and the content of iron is determined by analyzing the sample to be measured based on this calibration curve.

The alcohols, preferably ethanol, used in the present invention are not particularly limited, and are preferably alcohols using a gas containing carbon monoxide and hydrogen as a substrate, or alcohols produced using microorganism fermentation or a metal catalyst using sugar or cellulose as a raw material. In the case of these alcohols, it is convenient in the manufacturing process to adjust the iron content to the above-mentioned concentration. It was also found that commercially available non-fossil fuel derived ethanol, for example, sugar ethanol, and especially ethanol for use as a reagent in a small scale such as that described in known literature, did not contain Fe as described in the comparative example. Therefore, for industrial use as a chemical raw material, there is a need to control the Fe content strictly. In such case, the iron content may be adjusted to the above-described concentration by further purification, preferably by the purification method described herein. When iron is not contained exceeding the above concentration, the iron may be contained in a process for producing the ethanol from a raw material and/or before a process for converting the ethanol to a conjugated diene, and the timing of containing the iron is not particularly limited, and storage, transportation and delivery are also included. The method of containing Fe is not particularly limited, and may be, for example, addition or elution in contact with a metal containing Fe.

Without being bound by theory, by reducing the content of a specific metal in the ethanol to an extremely low value in the present invention, the butadiene selectivity in the synthesis of butadiene using the ethanol as a raw material can be improved, the yield in the synthesis of SBR can be improved, and the glass transition temperature of SBR and the butadiene/styrene ratio can be controlled.

The alcohol, particularly ethanol, used in the present invention may contain inorganic components other than Fe. For example, inorganic components such as Si, K, and Na may be contained. Compounds containing these elements may be inorganic compounds or organometallic compounds.

When Si is contained in the alcohol, particularly ethanol, the content of Si with respect to the ethanol is preferably 10 mg/L or more, more preferably 20 mg/L or more, still more preferably 30 mg/L or more, and preferably 100 mg/L or less, more preferably 90 mg/L or less, and still more preferably 80 mg/L or less. The Si content is the amount in Si element conversion of the Si compound. When the content of Si is in the above-mentioned numerical range, water produced by the butadiene synthesis reaction can be supplemented, so that the selectivity of butadiene in the synthesis of butadiene using the ethanol as a raw material can be improved and the yield of butadiene polymerization reaction can be improved.

The content of Si in the alcohol, particularly ethanol, can be measured by known methods. As a method of measuring the Si content, for example, a method of analyzing by using an inductively coupled plasma mass spectrometry (ICP-MS) can be mentioned. In the analytical method using ICP-MS, a standard solution for atomic absorption is analyzed after concentration adjustment to prepare a calibration curve, and the Si content is determined by analyzing the sample to be measured based on this calibration curve.

The alcohol, particularly ethanol, of the present invention is obtained by extracting and further purifying an ethanol-containing liquid obtained from a microbial fermentation tank as will be described later, and can contain other components in addition to the aforementioned unavoidable substances. For example, a small amount of an aromatic compound may be contained. Examples of the aromatic compound include toluene, ethylbenzene, o-xylene, m-xylene, and p-xylene, and only one or two or more of these may be included. The aromatic compound preferably includes ethylbenzene.

The content (total) of the aromatic compound contained in the alcohol, particularly ethanol, is preferably 0.4 mg/L or more, more preferably 0.5 mg/L or more, still preferably 0.7 mg/L or more, still more preferably 1.0 mg/L or more, and preferably 10 mg/L or less, more preferably 7 mg/L or less, still preferably 5 mg/L or less, and still more preferably 3 mg/L or less with respect to the total ethanol. When the content of the aromatic compound is in the above-range, the mixing of styrene and ethanol in the polymerization reaction becomes smooth, improving the yield of the polymerization reaction.

The content of the aromatic compound in the alcohol, particularly ethanol, can be measured by known methods. As a method for measuring the content of the aromatic compound, for example, a method using gas chromatography mass spectrometry (GC-MS) can be mentioned. In the analytical method using GC-MS, a calibration curve is prepared by analyzing the standard gas, and the content of aromatic compounds is determined by analyzing the sample to be measured based on this calibration curve.

When ethylbenzene is contained in the alcohol, particularly ethanol, the content of ethylbenzene is preferably 0.1 mg/L or more, more preferably 0.2 mg/L or more, still preferably 0.3 mg/L or more, still more preferably 0.5 mg/L or more, and preferably 5 mg/L or less, more preferably 3 mg/L or less, still preferably 2 mg/L or less, and still more preferably 1 mg/L or less, with respect to the total ethanol. When the content of ethylbenzene is in the above-mentioned numerical range, the mixing of styrene and ethanol in the polymerization reaction becomes smooth, improving the yield of the polymerization reaction.

The content of ethylbenzene in the alcohol, particularly ethanol, can be measured by known methods. As a method for measuring the content of ethylbenzene, for example, a method using gas chromatography mass spectrometry (GC-MS) can be mentioned. In the analytical method using GC-MS, a calibration curve is prepared by analyzing the standard gas, and the content of ethylbenzene is determined by analyzing the sample to be measured based on this calibration curve.

When toluene is contained in the alcohol, particularly ethanol, the content of toluene is preferably 0.01 mg/L or more, more preferably 0.02 mg/L or more, still preferably 0.03 mg/L or more, still more preferably 0.05 mg/L or more, and preferably 1 mg/L or less, more preferably 0.5 mg/L or less, still preferably 0.2 mg/L or less, and still more preferably 0.1 mg/L or less with respect to the total ethanol. When the content of toluene is in the above-mentioned numerical range, the mixing of styrene and ethanol in the polymerization reaction becomes smooth, improving the yield of the polymerization reaction.

The content of toluene in the ethanol can be measured by known methods. As a method for measuring the content of toluene, for example, a method using gas chromatography mass spectrometry (GC-MS) can be mentioned. In the analytical method using GC-MS, a calibration curve is prepared by analyzing the standard gas, and the content of toluene is determined by analyzing the sample to be measured based on this calibration curve.

When o-xylene is contained in the alcohol, particularly ethanol, the content of o-xylene is preferably 0.1 mg/L or more, more preferably 0.2 mg/L or more, still preferably 0.3 mg/L or more, still more preferably 0.5 mg/L or more, and preferably 5 mg/L or less, more preferably 3 mg/L or less, still preferably 2 mg/L or less, and still more preferably 1 mg/L or less, with respect to the total ethanol. When the content of o-xylene is in the above-mentioned numerical range, the mixing of styrene and ethanol in the polymerization reaction becomes smooth, improving the yield of the polymerization reaction.

The content of o-xylene in the alcohol, particularly ethanol, can be measured by a conventionally known method. As a method for measuring the content of o-xylene, for example, a method using gas chromatography mass spectrometry (GC-MS) can be mentioned. In the analytical method using GC-MS, a calibration curve is prepared by analyzing the standard gas, and the content of o-xylene is determined by analyzing the sample to be measured based on this calibration curve.

When m-xylene and/or p-xylene is contained in the alcohol, particularly ethanol, the content (sum) of m-xylene and/or p-xylene is preferably 0.1 mg/L or more, more preferably 0.2 mg/L or more, and preferably 5 mg/L or less, more preferably 3 mg/L or less, still preferably 2 mg/L or less, and still more preferably 1 mg/L or less, with respect to the total ethanol. When the content of m-xylene and/or p-xylene is in the above-mentioned numerical range, the mixing of styrene and ethanol in the polymerization reaction becomes smooth, improving the yield of the polymerization reaction.

The content of m- or p-xylene in the alcohol, particularly ethanol, can be determined by conventional methods. As a method for measuring the content of m- or p-xylene, for example, a method using gas chromatography mass spectrometry (GC-MS) can be mentioned. In the analytical method using GC-MS, a calibration curve is prepared by analyzing the standard gas, and the content of m- or p-xylene is determined by analyzing the sample to be measured based on this calibration curve.

When chlorine is contained in the alcohol, particularly ethanol, the content of the ethanol is preferably less than 2 mg/L. When chlorine is contained in an amount more than the above-mentioned range, the catalyst for the reaction of synthesizing butadiene from ethanol becomes deactivated, reducing the conversion of the ethanol.

The content of chlorine in the alcohol, particularly ethanol, can be measured by known methods. As a method of measuring the content of chlorine, for example, an analytical method using ion chromatography can be mentioned. In the method using ion chromatography, a calibration curve is prepared by analyzing the standard solution, and the content of chlorine is determined by analyzing the sample to be measured based on this calibration curve.

The alcohol, particularly ethanol, of the present invention contains inorganic components as above and trace optionally organic components such as aromatic hydrocarbons and aliphatic hydrocarbons; and the concentration of the ethanol (pure ethanol as a compound) as the main component in the ethanol is 75 vol % or more, preferably 80 vol % or more, more preferably 90 vol % or more, still preferably 95 vol % or more, still more preferably 98 vol % or more, and 99.999 vol % or less, more preferably 99.99 vol % or less, still preferably 99.9 vol % or less, and still more preferably 99.5 vol % or less, with respect to the total ethanol.

<Method for Producing Alcohol>

The method for producing an alcohol, particularly ethanol, having a specific inorganic/organic compound as described above is not particularly limited, as long as the content thereof falls within the range specified in the present invention; and examples of the raw material of the alcohol include biomass resources, specifically, cellulose plants (pulp, waste paper, paper, etc.), wood, charcoal, compost, natural rubber, cotton, sugar cane, okara (soy bean curd residue), oil and fat, plants (corn, cassava, bagasse, etc.), marine product residues, livestock excrement, waste, algae, and the like. The biomass resources may be those extracted and purified from the biomass resources as described above or the treated biomass resources (i.e. biomass-derived substances). For example, it may be sugar ethanol purified from these biomass resources. Preferably, the ethanol can be produced by microbial fermentation of a synthetic gas containing carbon monoxide derived from waste or an exhaust gas. In such a method, the content of the aromatic compound or the like in the raw material gas derived from the waste or the exhaust gas and the purification conditions may be controlled to control the amount of the aromatic compound, etc. contained in the final product. Hereinafter, a method for producing the ethanol by microbial fermentation of a synthetic gas containing carbon monoxide derived from waste or an exhaust gas will be described as one example.

The method for producing alcohol, particularly ethanol, comprises a step of converting a carbon source into a synthetic gas containing carbon monoxide and hydrogen; a microbial fermentation step in which the synthetic gas containing carbon monoxide and hydrogen is fed into a microbial fermentation tank for microbial fermentation to obtain an ethanol-containing liquid; a separation step in which the ethanol-containing liquid is separated into a liquid or solid constituent containing microorganisms and a gas constituent containing the ethanol; a liquefaction step in which the gas constituent is condensed and liquefied; and a purification step in which the ethanol is purified from the liquid obtained in the liquefaction step; and optionally may comprise a raw material gas generating step, synthetic gas preparation step, waste water treatment step, etc. Each step will be described below.

<Raw Material Gas Generating Step

The raw material gas generating step is a step of generating a raw material gas by gasifying a carbon source in the gasification unit. A gasification furnace may be used in the raw material gas generating step.

A gasification furnace is a furnace for burning (incompletely burning) a carbon source, examples thereof including a shaft furnace, a kiln furnace, a fluidized bed furnace, and a gasification reforming furnace. The gasification furnace is preferably a fluidized bed furnace type because a high hearth load and excellent operability can be achieved by partially combusting the waste. The waste is gasified in a fluidized bed furnace at a low temperature (about 450 to 600° C.) and in a low oxygen atmosphere to be decomposed into char containing a large amount of gas (carbon monoxide, carbon dioxide, hydrogen, methane, etc.) and carbon. In addition, since the incombustibles contained in the waste are separated from the bottom of the furnace in a hygienic and lightly oxidized state, valuable substances such as iron and aluminum in the incombustibles can be selectively recovered. Therefore, gasification of such waste enables efficient resource recycling.

The gasification temperature in the raw material gas generating step is usually, without particular limitation, 100 to 2500° C., preferably 200 to 2100° C.

The gasification reaction time in the raw material gas generating step is usually 2 seconds or more, preferably 5 seconds or more.

A carbon source used in the raw material gas generating step is not particularly limited, and for example, suitably used are coal used in a coke oven in a steel plant, a blast furnace (blast furnace gas), a converter or a coal-fired power plant, general waste and industrial waste introduced into an incinerator (especially a gasification furnace), carbon dioxide produced as a by-product by various industries, and also various carbon-containing materials and the like for the purpose of recycling.

More specifically, the carbon source is preferably waste, in particular, plastic waste, kitchen waste, municipal solid waste (MSW), industrial solid waste, waste tires, biomass waste, household waste such as duvet (futon) and paper, waste such as building materials, coal, petroleum, petroleum-derived compounds, natural gas, shale gas, and the like, among which various types of waste are preferable, and from the viewpoint of separation cost, the more preferred is unsorted municipal solid waste.

As for the carbon source, for example, a waste tire is used as a combustion material, specifically, use can be made to a gas generated when heat energy generated during combustion of the waste tire is recovered, such as thermal recycling. The combustion apparatus is not particularly limited, examples thereof including a blast furnace, a blast furnace (blast furnace gas), a converter used in a steel plant as above, a coal incinerator, a boiler used in a coal power plant, and the like. In particular, about 60% of the raw materials of the tires are suitable for combustion materials, and tire chips obtained from waste tires have a total calorific value of 35,000 kJ per 1 kg, which is almost the same as that of petroleum products such as light oil and heavy oil, thus the they are suitable for alternative fuels such as coal. That is, when $CO_2$ is used as the main gas, the gas generated in these processes is preferably converted into CO by using a known technique so that resource recycling can be achieved as an effective measure for reducing $CO_2$.

The raw material gas obtained by gasifying a carbon source contains carbon monoxide and hydrogen as essential components, and may further contain carbon dioxide, oxygen and nitrogen. As other components, the raw material gas may further contain components such as soot, tar, a nitrogen compound, a sulfur compound, and an aromatic compound.

The raw material gas may be produced as a gas containing carbon monoxide in an amount of, without particular limitation, 0.1 vol % or more, preferably 10 vol % or more, more preferably 20 vol % or more, by performing a heat treatment (commonly called gasification) for combusting (incomplete combustion) a carbon source in the raw material gas producing step, that is, by partially oxidizing the carbon source.

<Synthetic Gas Purification Step>

The synthetic gas purification step is a step of removing or reducing specific substances such as various pollutants, soot and dust particles, impurities and compounds in an undesirable amount from the raw material gas. In the case where the raw material gas is derived from waste, the raw material gas usually tends to contain carbon monoxide in an amount of 0.1 vol % to 80 vol %, carbon dioxide in an amount of 0.1 vol % to 70 vol %, hydrogen in an amount 0.1 vol % to 80 vol %, a nitrogen compound in an amount of 1 mg/L or more, a sulfur compound in an amount of 1 mg/L or more, a phosphorus compound in an amount of 0.1 mg/L or more, and/or an aromatic compound in an amount of 10 mg/L or more. It may also contain other environmental pollutants, soot and dust particles, and impurities. Therefore, when the synthetic gas is supplied to the microbial fermentation tank, it is preferable to reduce or remove substances that are not suitable for stable culturing of microorganisms and compounds in an undesirable amount, etc. from the raw material gas so that the content of each component contained in the raw material gas is in a range suitable for stable culturing of the microorganisms.

In particular, in the synthetic gas purification step, the carbon dioxide gas in the synthetic gas is adsorbed on the regenerated adsorbent (zeolite) by using the pressure swing adsorption apparatus filled with the regenerated adsorbent to reduce the concentration of the carbon dioxide gas in the synthetic gas. Further, the synthetic gas may be subjected to other conventional treatment steps to remove impurities and adjust the gas composition. As other treatment steps, for example, one or two or more of the following can be used: a gas chiller (water separator), low-temperature separation type (cryogenic separation type) separator, fine particle (soot) separator such as cyclone and bag filter, scrubber (water-soluble impurity separator), desulfurizer (sulfide separator), membrane separation type separator, deoxygenator, pressure swing adsorption type separator (PSA), temperature swing adsorption type separator (TSA), pressure swing adsorption type separator (PTSA), separator using activated carbon, deoxygenator, more specifically, a separator using copper or palladium catalysts.

In the present invention, the concentration of iron and chromium derived from the raw material gas can be controlled by adjusting the conditions of the above-described treatment steps. For example, these concentrations can be reduced to below the detection limit by adjusting conditions such as the residence time of the scrubber and the membrane separation. By reducing the concentration of iron and chromium in the raw material gas in this manner, the content of iron and chromium in the final alcohol, particularly ethanol, can be reduced to below the detection limit.

The synthetic gas used in the process for producing an alcohol, particularly ethanol, of the present invention contains at least carbon monoxide as an essential component and may further contain hydrogen, carbon dioxide and nitrogen.

The synthetic gas used in the present invention may be a gas obtained by carrying out the steps of gasifying a carbon source to generate a raw material gas (a raw material gas generating step), and then adjusting the concentration of each component of carbon monoxide, carbon dioxide, hydrogen, and nitrogen and reducing or removing the above-mentioned substances and compounds from the raw material gas.

The concentration of carbon monoxide in the synthetic gas is usually 20 vol % to 80 vol %, preferably 25 vol % to 50 vol %, more preferably 35 vol % to 45 vol %, with respect to the total concentration of carbon monoxide, carbon dioxide, hydrogen and nitrogen in the synthetic gas.

The concentration of hydrogen in the synthetic gas is usually 10 vol % to 80 vol % or less, preferably 30 vol % to 55 vol %, and more preferably 40 vol % to 50 vol % with respect to the total concentration of carbon monoxide, carbon dioxide, hydrogen, and nitrogen in the synthetic gas.

The concentration of carbon dioxide in the synthetic gas is usually 0.1 vol % to 40 vol %, preferably 0.3 vol % to 30 vol %, more preferably 0.5 vol % to 10 vol %, and particularly preferably 1 vol % to 6 vol %, with respect to the total concentration of carbon monoxide, carbon dioxide, hydrogen, and nitrogen in the synthetic gas.

The concentration of nitrogen in the synthetic gas is usually 40 vol % or less, preferably 1 vol % to 20 vol % or less, and more preferably 5 vol % to 15 vol % with respect to the total concentration of carbon monoxide, carbon dioxide, hydrogen, and nitrogen in the synthetic gas.

The concentration of carbon monoxide, carbon dioxide, hydrogen, and nitrogen can be set within a predetermined range by changing the element composition of the carbon hydride (carbon and hydrogen) and nitrogen in the carbon source in the raw material gas generating step or by changing the combustion conditions such as the combustion temperature and the oxygen concentration of the supply gas during combustion if necessary. For example, in the case where the concentration of carbon monoxide or hydrogen is to be changed, a carbon source having a high carbon hydride (carbon and hydrogen) ratio such as waste plastic may be used, and in the case where the concentration of nitrogen is to be lowered, a gas having a high oxygen concentration may be supplied in the raw material gas generating step.

The synthetic gas used in the present invention is not particularly limited but may contain a sulfur compound, a phosphorus compound, a nitrogen compound and the like in addition to the above-described components. The content of each of these compounds is preferably 0.05 mg/L or more, more preferably 0.1 mg/L or more, still more preferably 0.5 mg/L or more, and preferably 2000 mg/L or less, more preferably 1000 mg/L or less, still preferably 80 mg/L or less, still more preferably 60 mg/L or less, and particularly preferably 40 mg/L or less. When the content of the sulfur compound, the phosphorus compound, the nitrogen compound, and the like is not less than the lower limit, there is an advantage that the microorganisms can be suitably cultured, and when the content is not more than the upper limit, there is an advantage that the culture medium is not contaminated by various nutrition sources which the microorganisms have not consumed.

Examples of the sulfur compound include sulfur dioxide, $CS_2$, $COS$, and $H_2S$, and preferred amongst them are $H_2S$ and sulfur dioxide as they are easily consumed as a nutrition source for the microorganisms. Therefore, it is more preferable that the synthetic gas contains the sum of $H_2S$ and sulfur dioxide within the above ranges.

As the phosphorus compound, phosphoric acid is preferred as it is easily consumed as a nutrition source for the microorganisms. Therefore, it is more preferable that the synthetic gas contains phosphoric acid within the above ranges.

Examples of the nitrogen-containing compound include nitrogen monoxide, nitrogen dioxide, acrylonitrile, acetonitrile, HCN, and the like, and HCN is preferable in that it is easily consumed as a nutrient source for the microorganisms. Therefore, it is more preferable that the synthetic gas contains HCN in the above range.

The synthetic gas may contain an aromatic compound in the amount of 0.001 mg/L to 90 mg/L, preferably 0.03 mg/L or more, more preferably 0.05 mg/L or more, and still preferably 0.1 mg/L or more, and preferably 70 mg/L or less, more preferably 50 mg/L or less, and still preferably 30 mg/L or less. When the content is not less than the lower limit, the microorganisms tend to be cultured suitably, and when the content is not more than the upper limit, the culture medium tends to be less contaminated by various nutrition sources which the microorganisms have not consumed.

<Microbial Fermentation Step>

The microbial fermentation step is a step of producing alcohol, particularly ethanol, by microbial fermentation of the synthetic gas in a microbial fermentation tank. The microbial fermentor is preferably a continuous fermentor. Generally, the microbial fermenter may be of any shape, and examples thereof include a stirring type, an airlift type, a bubble column type, a loop type, an open-bond type, and a photobio type, and in the present invention, preferred use is made to a known loop reactor in which the microbial fermentation tank is equipped with a main tank portion and a reflux portion. In this case, it is preferable to further comprise a circulation step of circulating the liquid medium between the main tank portion and the reflux portion.

As the synthetic gas to be supplied to the microbial fermentation vessel, the gas obtained through the raw material gas generating step may be used as it is as long as the composition conditions of the synthetic gas are satisfied, or the synthetic gas may be used by adding another predetermined gas to the gas obtained by reducing or removing impurities and the like from the raw material gas. As another predetermined gas, for example, at least one of the compounds selected from the group consisting of sulfur compounds such as sulfur dioxide, phosphorus compounds, and nitrogen compounds may be added to form a synthetic gas.

Although the synthetic gas and the microbial culture liquid may be continuously fed into the microbial fermentation vessel, the synthetic gas and the microbial culture liquid need not be fed simultaneously, and the synthetic gas may be fed to the microbial fermentation vessel to which the microbial culture liquid has been previously fed. It is known that some anaerobic microorganisms produce alcohols, particularly ethanol, from a substrate gas such as the synthetic gas by the fermenting action, and these gas-utilizing microorganisms are cultured in a liquid medium. For example, the liquid medium and the gas-utilizing bacteria may be fed and stored, and while the liquid medium is stirred in this state, the synthetic gas may be fed into the microbial fermentation vessel. Accordingly, the gas-utilizing bacteria can be cultured in a liquid medium and by the fermenting action, ethanol can be produced from the synthetic gas.

The temperature of the medium (culture temperature) in the microbial fermentation vessel may be of any temperature, preferably about 30 to 45° C., more preferably about 33 to 42° C., still more preferably about 36.5 to 37.5° C. The culture time is preferably 12 hours or more, more preferably 7 days or more, particularly preferably 30 days or more, and most preferably 60 days or more in a continuous culture, and the upper limit is not particularly determined, preferably 720 days or less, more preferably 365 days or less from the viewpoint of regular maintenance of equipment. The culture time means the time from the addition of the seed bacteria to the culture tank to the discharge of the entire culture liquid in the culture tank.

The microorganisms (species) contained in the microbial culture liquid are not particularly limited as long as they can produce ethanol by microbial fermentation of the synthetic gas using carbon monoxide as the main raw material. For example, the microorganisms (species) are preferably microorganisms which generate ethanol from the synthetic gas by the fermenting action of gas-utilizing bacteria, and particularly preferably microorganisms having a metabolic pathway of acetyl CoA. Among the gas-utilizing bacteria, the genus *Clostridium* is more preferred, and *Clostridium autoethanogenum* is particularly preferred, without particular limitation. The following is a further example.

Gas-utilizing bacteria include both eubacteria and archaebacteria. Examples of the eubacteria include *Clostridium, Moorella, Acetobacterium, Carboxydocella, Rhodopseudomonas, Eubacterium, Butyribacterium, Oligotropha, Bradyrhizobium*, and aerobic hydrogen-oxidizing bacteria, *Ralsotonia* bacteria, and the like.

On the other hand, examples of the archaebacteria include bacteria from the genus of *Methanobacterium, Methanobrevibacter, Methanocalculus, Methanococcus, Methanosarcina, Methanosphaera, Methanothermobacter, Methanothrix, Methanoculleus, Methanofollis, Methanogenium, Methanospirillium, Methanosaeta, Thermococcus, Thermofilum, Arcaheoglobus*, and the like. Amongst these, preferred as the archaebacterial are *Methanosarcina, Methanococcus, Methanothermobacter, Methanothrix, Thermococcus, Thermofilum*, and *Archaeoglobus*.

Further, preferred as the archaebacteria are bacteria from the genus of *Methanosarcina, Methanothermobactor*, or *Methanococcus*, and particularly preferred are *Methanosarcina* or *Methanococcus*, due to excellent carbon monoxide and carbon dioxide utilizing properties. Specific examples of the bacteria from the genus of *Methanosarcina* include *Methanosarcina barkeri, Methanosarcina mazei, Methanosarcina acetivorans*, and the like.

Among the above gas-utilizing bacteria, bacteria having a high ability to produce the ethanol of interest are selected and used. For example, the gas-utilizing bacteria having a high ethanol-producing ability include *Clostridium autoethanogenum, Clostridium I jungdahlii, Clostridium aceticum, Clostridium carboxidivorans, Moorella thermoacetica, Acetobacterium woodii*, and among these, *Clostridium autoethanogenum* is particularly preferable.

The medium used for culturing the microorganism (species) is not particularly limited as long as it has an appropriate composition corresponding to the microorganism, and is a liquid containing water as a main component and a nutrient (for example, vitamin, phosphoric acid, etc.) dissolved or dispersed in the water. The composition of such a medium is prepared so that gas-utilizing bacteria can grow well. For example, as a culture medium in the case of using *Clostridium* for microorganisms, reference can be made to U.S. Patent Application Publication No. 2017/260552, [0097] to [0099], etc.

The alcohol-containing liquid, particularly the ethanol-containing liquid, obtained by the microbial fermentation step can be obtained as a suspension containing microorganisms, dead microorganisms, proteins derived from microorganisms, and the like. The protein concentration in the suspension varies depending on the type of the microorganisms, but is usually 30 to 1000 mg/L. The protein concentration in the ethanol-containing solution can be measured by the Kjeldahl method.

<Separation Step>

The alcohol-containing liquid, particularly the ethanol-containing liquid, obtained by the microbial fermentation step is then subjected to a separation step. In the present invention, the ethanol-containing liquid is heated to room temperature to 500° C. under the condition of 0.01 to 1000 kPa (absolute pressure) to separate the liquid or solid constituent containing microorganisms from the gas constituent containing the ethanol. In the conventional method, the ethanol-containing liquid obtained in the microbial fermentation step is distilled to separate and purify the desired ethanol; however since the ethanol-containing liquid contains microorganisms, proteins derived from microorganisms, and the like, foaming occurs in the distillation apparatus to interfere the continuous operation when the ethanol-containing liquid is distilled as it is. Although it is known to use a membrane evaporator as a method for purifying a foaming liquid, the membrane evaporator is low in concentration efficiency and is not suitable for purifying a liquid containing a solid constituent. In the present invention, the ethanol-containing liquid is heated before the desired ethanol is separated and purified from the ethanol-containing liquid obtained by the microbial fermentation step by a distillation operation, etc. and is separated into a liquid or solid constituent containing the microorganisms and a gas constituent containing ethanol, and the desired ethanol is separated and purified from only the separated gas constituent containing ethanol. By performing the separation step, foaming does not occur in the distillation apparatus in the distillation operation at the separation and purification of the ethanol, so that the distillation operation can be carried out continuously. Further, since the concentration of the ethanol contained in the gas constituent containing the ethanol becomes higher than the concentration of the ethanol in the ethanol-containing liquid, the ethanol can be efficiently separated and purified in a purification step to be described later.

In the present invention, from the viewpoint of efficiently separating the liquid or solid constituent containing the microorganisms, dead microorganisms, proteins derived from the microorganisms, etc. from the gas constituent containing ethanol, the ethanol-containing liquid is heated preferably at a temperature of 50 to 200° C., more preferably at a temperature of 80 to 180° C., still preferably at a temperature of 100 to 150° C. under the conditions of 10 to 200 kPa, more preferably 50 to 150 kPa, and still more preferably under normal pressure.

The heating time in the separation step is not particularly limited as long as the gas constituent can be obtained, and from the viewpoint of efficiency or economy, the heating time is usually 5 seconds to 2 hours, preferably 5 seconds to 1 hour, more preferably 5 seconds to 30 minutes.

In the above-described separation step, any device can be used that is capable of efficiently separating the ethanol-containing liquid into liquid or solid constituent (microorganisms, dead microorganisms, proteins derived from microorganisms, etc.) and the gas constituent (ethanol) using thermal energy without any particular limitation, and for example, a drying device such as a rotary dryer, a fluidized bed dryer, a vacuum dryer, or a conductive heating dryer can be used, and in view of efficiency in separating the liquid or solid constituent and the gas constituent from the ethanol-containing liquid in which the solid constituent concentration is low, the use of the conductive heating dryer is preferred. Examples of the conductive heating dryer include a drum type dryer and a disk type dryer.

<Liquefaction Step>

The liquefaction step is a step of liquefying the gas constituent containing alcohol, particularly ethanol, obtained in the above-described separation step by condensation. The apparatus used in the liquefaction step is not particularly limited, and a heat exchanger, particularly a condenser, is preferably used. Examples of the condenser include a water-cooled type, an air-cooled type, and an evaporation type, among which a water-cooled type is preferable. The condenser may be one-stage or a multi-stage condenser.

Although it can be said that it is preferable that the components contained in the ethanol-containing liquid, such as the microorganisms, dead microorganisms, or proteins derived from the microorganisms, are not contained in the liquid obtained by the liquefaction step, the present invention does not exclude the presence of a protein in the liquid. Even when a protein is contained in the liquid, the concentration thereof is preferably 40 mg/L or less, more preferably 20 mg/L or less, still more preferably 15 mg/L or less.

The condensation heat of the gas constituent obtained by the condenser may be reused as a heat source in a purification step described later. The ethanol can be produced efficiently and economically by the reuse of the condensation heat.

<Purification Step>

Next, alcohol is purified from the liquefied product obtained in the liquefaction step. This production method differs depending on the alcohol; however there is no particular limitation as long as the specific compound defined in the present invention is limited to a specific content. The purification process in the ethanol is described in detail below. The ethanol-containing liquid obtained in the microbial fermentation step can be fed to the purification step without undergoing the above-described separation step when components such as the microorganisms have already been removed. The purification step is a step of separating the ethanol-containing liquid obtained in the liquefaction step into a distillate having a higher concentration of the target ethanol and a bottom content having a lower concentration of the target ethanol. The purification step described in the present specification to produce the ethanol defined by the present invention may also be carried out for ethanol produced from other than the synthetic gas as described above or in commercially available bioethanol. Examples of the apparatus used in the purification step include a distillation apparatus, a treatment apparatus including a osmotic evaporating membrane, a treatment apparatus including a zeolite dehydration membrane, a treatment apparatus for removing a low boiling point substance having a boiling point lower than that of ethanol, a treatment apparatus for removing a high boiling point substance having a boiling point higher than that of ethanol, and a treatment apparatus including an ion exchange membrane. These apparatuses may be used alone or two or more of these in combination. As the unit operation, thermal distillation or membrane separation may be suitably used.

In the thermal distillation, the desired ethanol can be obtained as a distillate with high purity by using a distillation apparatus. The temperature in the distillation apparatus during the distillation of the ethanol is, without particular limitation, preferably 100° C. or lower, more preferably about 70 to 95° C. By setting the temperature in the distillation apparatus within the above range, the separation of the ethanol from other components, i.e., the distillation of the ethanol can be performed more reliably. In particular, high-purity ethanol can be obtained by introducing the ethanol-containing liquid obtained in the liquefaction step into a distillation apparatus equipped with a heater using steam of 100° C. or higher, raising the temperature at the bottom of the distillation column to 90° C. or higher within 30 minutes, subsequently introducing the ethanol-containing liquid from the middle of the distillation column, and performing the distillation step in which the temperature difference of the bottom, middle, and top of the column is within f 15° C. The distillation temperature difference is preferably f 13° C., more preferably f 11° C. When the distillation temperature difference is set as above, separation from other components, i.e., distillation of the ethanol can be performed more reliably, which is preferable for producing ethanol defined in the present invention.

Without being bound by theory, it is believed that the ethanol-containing liquid contains Si in the form of an organosiloxane (e.g., 1,1,3,3-tetramethyldisiloxane, hexamethyldisiloxane, etc.) having a boiling point of 100° C. or lower. The ethanol obtained by distillation of such ethanol can contain a trace amount of Si by allowing the organosiloxane having a boiling point close to that of the ethanol remain. In the present invention, the Si content in ethanol contained in the distillate can be adjusted by adjusting the distillation conditions described above. As a result, the Si content in the final ethanol can be adjusted. In the above separation step, the Si content in the final ethanol can also be adjusted by stabilizing the organosiloxane in the synthetic gas by maintaining the gas introduction temperature to the separator at 20° C. to 40° C.

As the distillation apparatus, it is preferable to use a plurality of distillation columns. In this case, it is preferable to use a treatment apparatus including an ion exchange membrane between the distillation columns. In the present invention, the concentration of sodium ions and potassium ions are controlled by conducting distillation through the ion exchange membrane, and as a result, the sodium content and the potassium content in the final ethanol can be adjusted to a suitable range.

The ethanol-containing liquid is considered to contain an aliphatic hydrocarbon having a boiling point higher than that of the ethanol (for example, heptane, octane, decane, dodecane, tetradecane, etc.), an aromatic compound (for example, toluene, ethylbenzene, xylene, etc.), and dialkyl ether (for example, dibutyl ether, dipentyl ether, etc.). In the present invention, by adjusting the distillation conditions described above (for example, the aromatic compounds are also distilled out by making the temperature of the uppermost portion of the distillation column to a temperature 5 to 10° C. or higher than usual), the aromatic compounds in the ethanol contained in the distillate can be adjusted. As a result, the content of the aromatic compound in the final ethanol can be adjusted.

The pressure in the distillation apparatus during distillation of the ethanol may be at an atmospheric pressure; however, preferred is less than the atmospheric pressure, more preferably about 60 to 95 kPa (absolute pressure). By setting the pressure in the distillation apparatus to the above range, the separation efficiency of the ethanol can be improved, leading to improvement in the yield of the ethanol, which is preferable for producing the ethanol defined by the invention. The yield of the ethanol (the concentration of the ethanol contained in the distillate after distillation) is preferably 90 vol % or more, more preferably 95 vol % or more.

In the membrane separation, a known separation membrane can be suitably used, for example, a zeolite membrane can be suitably used.

The concentration of the ethanol contained in the distillate separated in the purification step is preferably 20 vol % to 99.99 vol %, more preferably 60 vol % to 99.9 vol %.

On the other hand, the concentration of the ethanol contained in the bottom product is preferably 0.001 vol % to 10 vol %, more preferably 0.01 vol % to 5 vol %.

The bottom product separated in the purification step is substantially free of nitrogen compounds. In the present invention, "substantially free" does not mean that the concentration of the nitrogen compounds is 0 mg/L, but means that the concentration of the nitrogen compounds in the bottom product obtained in the purification step is such that there is no need for a waste water treatment step. In the separation step, the desired ethanol is not purified from the ethanol-containing liquid obtained in the microbial fermentation step, but instead, the ethanol-containing liquid is separated into a liquid or solid constituent containing the microorganisms and a gas constituent containing the ethanol as described above. At this time, since the nitrogen compound remains on the liquid constituent side or solid constituent side containing the microorganisms, the gas constituent containing the ethanol contains almost no nitrogen compound. Therefore, the bottom product obtained when the ethanol is purified from a liquefied product obtained by liquefying a gas constituent is considered to be substantially free of the nitrogen compound. Even when the nitrogen compound is contained in the bottom product, the concentration of the nitrogen compound is 0.1 to 200 mg/L, preferably 0.1 to 100 mg/L, more preferably 0.1 to 50 mg/L.

For the same reason as described above, the bottom product separated in the purification step is substantially free of a phosphorus compound. The expression "substantially free" does not mean that the concentration of the phosphorus compound is 0 mg/L, but means that the concentration of the phosphorus compound in the bottom product obtained in the purification step is such that there is no need for a wastewater treatment step. Even when the phosphorus compound is contained in the bottom product, the concentration of the phosphorus compound is 0.1 to 100 mg/L, preferably 0.1 to 50 mg/L, more preferably 0.1 to 25 mg/L. As described above, according to the method of the present invention, since the bottom product discharged in the ethanol purification step is considered substantially free of a nitrogen compound or a phosphorus compound, and hardly contains other organic substances, the waste water treatment step which has been conventionally required can be simplified.

<Wastewater Treatment Step>

The bottom product separated in the purification step may be fed to a waste water treatment step. In the waste water treatment step, organic substances such as nitrogen compounds and phosphorus compounds can be further removed from the bottom product. In this step, organic substances may be removed by treating the bottom product anaerobically or aerobically. The removed organic substance may be used as a fuel (heat source) in the purification step.

The treatment temperature in the waste water treatment step is usually 0 to 90° C., preferably 20 to 40° C., more preferably 30 to 40° C.

Since the bottom product obtained through the separation step is being removed of the liquid or solid constituent containing microorganisms, etc. there is less burden such as the waste water treatment than the bottom product obtained upon being directly fed from the microbial fermentation step to the purification step.

In the waste water treatment step, the concentration of the nitrogen compound in the treatment liquid obtained by treating the bottom product is preferably 0.1 to 30 mg/L, more preferably 0.1 to 20 mg/L, still more preferably 0.1 to 10 mg/L, and it is particularly preferable that no nitrogen compound is contained. The concentration of the phosphorus compound in the treatment liquid is preferably 0.1 to 10 mg/L, more preferably 0.1 to 5 mg/L, still more preferably 0.1 to 1 mg/L, and it is particularly preferable that no phosphorus compound is contained in the bottom product.

<Use of Alcohol>

Hereinafter, a method for synthesizing butadiene using an alcohol, particularly ethanol, of the present invention as a raw material, and a method for producing styrene-butadiene rubber (SBR) will be described by way of example; however it goes without saying that the method can also be used for a chemical product or a polymer raw material using other conjugated diene compounds.

<Synthesis of 1,3-Butadiene>

Butadiene is produced by refining C4 fraction that is subgenerated mainly when synthesizing (i.e., naphtha cracking) ethylene from petroleum, and is a raw material for synthetic rubber. However, there is a need in recent years for a technology for converting the ethanol (ethanol derived from microbial fermentation) that is not derived from fossil fuels into 1,3-butadiene, instead of chemical industrial raw materials obtained from petroleum. As a method for synthesizing butadiene using the ethanol derived from microbial fermentation as a raw material, there is known a method using MgO as a catalyst, a method using a mixture of $Al_2O_3$ and ZnO, a catalyst having a magnesium silicate structure, and the like. As the catalyst, hafnium, vanadium, manganese, iron, cobalt, nickel, copper, zinc, gallium, niobium, silver, indium, cerium, and the like are used.

The ethanol of the present invention is brought into contact with the above-mentioned catalyst and heated to cause ethanol conversion reaction, and as a result, 1,3-butadiene can be synthesized. Synthesizing 1,3-butadiene using the ethanol of the present invention as a raw material makes it possible to realize an ultimate resource recycling society independent of petroleum resources.

The heating temperature for accelerating the conversion reaction is, for example, about 200 to 450° C. and preferably 300 to 400° C. in the reaction system. When the temperature in the reaction system falls below the above ranges, the catalyst activity cannot be sufficiently obtained, decreasing the reaction rate, and the production efficiency tends to decrease. On the other hand, if the temperature in the reaction system exceeds the above ranges, the catalyst may be easily deteriorated.

The reaction can be carried out by a conventional method such as a batch method, a semi-batch method, and a continuous method. When the batch or semi-batch method was employed, the conversion rate of the ethanol can be increased; however, according to the ethanol of the present invention, it can be converted more efficiently than the conventional types even when the continuous method was employed. This reason is not clear; however, it is considered that the ethanol derived from a circulating resource using gas containing carbon monoxide and hydrogen as a substrate as like the present invention has a characteristic peak which cannot be observed in the ethanol derived from fossil fuels in a gas chromatograph measured by a gas chromatography mass spectrometry.

Examples of the method for bringing the raw material into contact with the catalyst can include a suspended bed method, a fluidized bed method, a fixed bed method, etc. The method may be either a vapor phase method or a liquid phase method. In view of convenience in recovery and regeneration of the catalyst, preferred is the use of a fixed bed reaction device for gas-phase continuous flow in which the catalyst is charged into a reaction tube to form a catalyst layer and the raw material is passed through as a gas in order to react with the gas phase. When the reaction is carried out in the gas phase, the ethanol of the present invention may be gasified and supplied to the reactor without dilution, or may be diluted appropriately with an inert gas such as nitrogen, helium, argon, carbon dioxide, etc. and supplied to the reactor.

After completion of the conversion reaction of the ethanol, the reaction product (1,3-butadiene) can be separated and purified by, for example, a method in which gas-liquid separation is carried out at 10° C. to extract only the gas, a method in which a reaction product is brought into contact with a drying material such as calcium chloride or molecular sieve, a separation means such as filtration, concentration, distillation, extraction, or a combination thereof.

The purity of the obtained butadiene is preferably 70% or more, more preferably 75% or more, still preferably 80% or more, and still more preferably 82% or more. This is because the yield of the polymerization reaction is improved. The purity of butadiene can be calculated by the following formula. Butadiene purity=concentration of butadiene/total organic compound purity The ratio of the concentration of the obtained butadiene to the concentration of the oxygen-containing compound is preferably 3 or more. This is to prevent deactivation of the catalyst used in the polymerization reaction. The ratio between the concentration of butadiene and the concentration of the oxygen-containing compound can be calculated by the following formula.

Butadiene/oxygen-containing compound=butadiene concentration/(ethanol concentration+ acetaldehyde concentration+ acetic acid concentration+ ethyl acetate concentration+ diethyl ether concentration)

The ratio of the concentration of the obtained butadiene to the concentration of the hydrocarbon compound is preferably 5 or more. This is to increase the purity of the polymer. The ratio between the concentration of butadiene and the concentration of hydrocarbon compound can be calculated by the following formula.

Butadiene/hydrocarbon compound=butadiene concentration/(ethylene concentration+ butene concentration+ propylene concentration+ butane concentration)

<Method for Producing Conjugated Diene Polymer>

The method for producing a conjugated diene polymer of the present invention comprises the steps of:

using an alcohol derived from a non-petrochemical raw material having an iron content of 0.0001 mg/L to 2 mg/L as a raw material, bringing said alcohol into contact with a catalyst and heating the alcohol to produce a conjugated diene having $C_4$ to $C_{12}$ carbons; and polymerizing the monomer comprising the conjugated diene to produce a non-petrochemical derived conjugated diene polymer.

The raw material used in the process for producing the conjugated diene is not particularly limited as long as it is an alcohol derived from a non-petrochemical raw material having an iron content of 0.0001 mg/L to 2 mg/L, and for example, the above-mentioned ethanol can be used.

Examples of the conjugated diene having $C_4$ to $C_{12}$ carbons obtained in the process for producing the conjugated diene include 1,3-butadiene, isoprene, 1,3-pentadiene, 2,3-dimethyl-1,3-butadiene, 2-methyl-1,3-pentadiene, 1,3-hexadiene, 4,5-diethyl-1,3-octadiene, and 3-butyl-1,3-octadiene. Among these, 1,3-butadiene is preferable. One of these conjugated dienes may be used alone or two or more in combination in the manufacturing process of the non-petrochemical derived conjugated diene polymer.

In the step of producing the conjugated diene polymer, only a conjugated diene having $C_4$ to $C_{12}$ carbons may be used as the monomer, or an aromatic hydrocarbon may be used in addition to the conjugated diene. Examples of the aromatic hydrocarbon used as the monomer include styrene, methylstyrene, ethylstyrene, t-butylstyrene, α-methylstyrene, α-methyl-p-methylstyrene, chlorostyrene, bromostyrene, methoxystyrene, dimethylaminomethylstyrene, dimethylaminoethylstyrene, diethylaminomethylstyrene, diethylaminoethylstyrene, cyanoethylstyrene, and vinylnaphthalene. Among these, styrene is preferable.

In the step of producing the conjugated diene polymer, the polymerization method of the monomer is not particularly limited, and the polymerization can be carried out by a known method. The polymerization method may be emulsion polymerization or solution polymerization. Emulsion polymerization is a method in which a poorly-soluble monomer in a solvent and an emulsifying agent (surfactant) are mixed in a conventionally known solvent such as water, and a polymerization initiator soluble in the solvent is added to perform polymerization. Solution polymerization is a method in which a monomer and a polymerization initiator are added to an inert solvent to perform polymerization.

The surfactant used in the process for producing the conjugated diene polymer is not particularly limited as long as it is generally used in emulsion polymerization. Specific examples of the surfactant include a cationic surfactant and an anionic surfactant.

In the process for producing the conjugated diene, the catalyst is not particularly limited, and a conventionally known catalyst can be used. For example, those preferably used as the polymerization catalyst are a catalyst containing a rare earth element-containing compound, a coordination catalyst using a metallocene catalyst, and an anionic polymerization catalyst using an organic metal compound.

The inert solvent used in the process for producing the conjugated diene polymer is generally used in solution polymerization and is not particularly limited as long as it does not inhibit the polymerization reaction. Specific examples of the inert solvent include chain aliphatic hydrocarbons such as butane, pentane, hexane, and heptane; alicyclic hydrocarbons such as cyclopentane and cyclohexane; and aromatic hydrocarbons such as benzene, toluene, and xylene. One of these inert solvents may be used alone or two or more in combination.

The polymerization initiator used in the process for producing the conjugated diene polymer is not particularly limited as long as it can polymerize the monomer containing a conjugated diene having $C_4$ to $C_{12}$ carbons. Specific examples thereof include a polymerization initiator using an organic alkali metal compound, an organic alkaline earth metal compound, a lanthanide metal compound, etc. as a main catalyst. Examples of the organic alkali-metal compound include organic monolithium compounds such as n-butyllithium, sec-butyllithium, t-butyllithium, hexyllithium, phenyllithium, and stilbenelithium; organic polyvalent lithium compounds such as dilithiomethane, 1,4-dilithiobutane, 1,4-dilithio-2-ethylcyclohexane, 1,3,5-trilithiobenzene, and 1,3,5-tris(lithiomethyl)benzene; organic sodium compounds such as sodium naphthalene; and organic potassium compounds such as potassium naphthalene. Examples of the organic alkaline earth compounds include di-n-butylmagnesium, di-n-hexylmagnesium, diethoxycalcium, calcium distearate, di-t-butoxystrontium, diethoxybarium, diisopropoxybarium, diethylmercaptobarium, di-t-butoxybarium, diphenoxybarium, diethylaminobarium, barium distearate, and dimethylbarium. Examples of the polymerization initiator using lanthanum-based metal compounds as a main catalyst include a polymerization initiator using lanthanum-based metals such as lanthanum, cerium, praseodymium, neodymium, samarium, gadolinium, and lanthanum-based metal salts consisted of a carboxylic acid, a phosphorus-containing organic acid, etc. as a main catalyst, and together with these, polymerization initiators consisted of promoters such as an alkylaluminum compound, an organoaluminum hydride compound, or an organoaluminum halide compound. Among these polymerization initiators, an organic monolithium compound and an organic polyvalent lithium compound are preferably used, more preferably, an organic monolithium compound, and particularly preferably, n-butyllithium. The organic alkali-metal compound may be used as an organic alkali-metal amide compound by reacting with the compound with secondary amine compounds such as dibutylamine, dihexylamine, dibenzylamine, pyrrolidine, piperidine, hexamethyleneimine, and heptamethyleneimine, beforehand. By using an organic alkali metal amide compound as a polymerization initiator, it is possible to make the obtained rubber cross-linked product to have improved low heat generation property and excellent wet grip property. One of these polymerization initiators may be used alone or two or more in combination.

The amount of the polymerization initiator to be used may be determined depending on the molecular weight of the desired conjugated diene polymer, and is usually in the range of 1 to 50 mmol, preferably 1.5 to 20 mmol, and more preferably 2 to 15 mmol per 1000 g of the monomer.

The polymerization temperature is usually in the range of −80 to +150° C., preferably 0 to 100° C., and more preferably 30 to 90° C. The polymerization mode can be either batch or continuous, and in the case of copolymerization of a conjugated diene compound and an aromatic vinyl compound, a batch type is preferred from the viewpoint of easily controlling the randomness of the bond between the conjugated diene monomer unit and the aromatic vinyl monomer unit.

Examples of the conjugated diene polymer obtained by the production method of the present invention include isoprene rubber (IR), butadiene rubber (BR), styrene butadiene rubber (SBR), chloroprene rubber (CR), and acrylonitrile butadiene rubber (NBR). Among these, styrene-butadiene rubber is preferable as the rubber component used for tires.

The weight average molecular weight (Mw) of the conjugated diene polymer obtained by the production method of the present invention is not particularly limited, and the value measured by gel permeation chromatography converted in polystyrene is preferably 100,000 to 2,000,000, more preferably 150,000 to 1,500,000, and particularly preferably 200,000 to 1,000,000. By setting the weight-average molecular weight (Mw) of the conjugated diene polymer having an active terminal in the above range, the obtained cross-linked rubber product can have a good balance between wet grip property and low heat generation property.

The molecular weight distribution expressed by the ratio (Mw/Mn) of the weight average molecular weight (Mw) and the number average molecular weight (Mn) of the conjugated diene polymer obtained by the production method of the present invention is preferably, without particular limitation, 4.0 to 6.0 and more preferably 4.7 to 6.0. When the molecular weight distribution (Mw/Mn) of the conjugated diene polymer is within the above range, it is possible to improve the low heat generation property of the resulting cross-linked rubber product.

The glass transition temperature (Tg) of the conjugated diene polymer obtained by the production method of the present invention is preferably, without particular limitation, −40° C. to −50° C., more preferably −41° C. to −47° C. The glass transition temperature of the conjugated diene polymer obtained by the production method of the present invention can be adjusted, for example, by changing the blending ratio of the conjugated diene monomer and the aromatic hydrocarbon monomer in the conjugated diene polymer.

The conjugated diene polymer thus obtained by the production method of the present invention can be suitably used in various applications after adding a filler, a cross-linking agent and the like. In particular, when silica is blended as a filler, a rubber composition can be obtained which can provide a cross-linked rubber having low heat generation and excellent wet grip properties.

<Rubber Composition>

The rubber composition of the present invention contains as a rubber component, a conjugated diene polymer obtained by the production method of the present invention described above and a filler. The filler is not particularly limited, and examples thereof include silica, carbon black, calcium carbonate, talc and the like.

Examples of the silica to be blended in the rubber composition include dry type white carbon, wet type white carbon, colloidal silica, precipitated and the like. Among these, wet type white carbon containing hydrated silicic acid as a main component is preferred. A carbon-silica dual phase filler in which silica is supported on the surface of the carbon black may also be used. Each of these silicas may be used alone or two or more of these in combination. The nitrogen adsorption specific surface area (measured by the BET method according to ASTM D 3037-81) of the silica used is preferably 50 to 300 $m^2/g$, more preferably 80 to 220 $m^2/g$. The pH of the silica is preferably 5 to 10.

The amount of silica contained in the rubber composition is 10 to 200 parts by weight, preferably 30 to 150 parts by weight, and more preferably 50 to 100 parts by weight with respect to 100 parts by weight of the rubber component in the rubber composition. By making the amount of silica to be contained in the above-mentioned range, the rubber composition can have excellent processability, and thus the obtained cross-linked rubber can have further improved wet grip property and low heat generation property.

The method for adding silica to the rubber composition is not particularly limited, and a method of adding silica to a solid conjugated diene polymer and kneading the polymer (dry kneading method) can be applied or a method of adding silica to a solution containing the conjugated diene polymer and solidifying and drying the solution (wet kneading method).

The carbon black blended in the rubber composition is not particularly limited, and examples thereof include furnace black, acetylene black, thermal black, channel black, and graphite. The blending of carbon black provides reinforcement and particularly improves the abrasion resistance.

The rubber composition of the present invention may further contain a silane coupling agent from the viewpoint of further improving the low heat generation property. The silane coupling agent is not particularly limited, and various silane coupling agents can be used. As the silane coupling agent, any silane coupling agent conventionally used in combination with silica in the rubber industry can be used, examples being, bis(3-triethoxysilylpropyl)tetrasulfide, bis(2-triethoxysilylethyl)tetrasulfide, bis(4-triethoxysilylbutyl)tetrasulfide, bis(3-trimethoxysilylpropyl)tetrasulfide, bis(2-trimethoxysilylethyl)tetrasulfide, bis(4-trimethoxysilylbutyl)tetrasulfide, bis(3-triethoxysilylpropyl)trisulfide, bis(2-triethoxysilylethyl)trisulfide, bis(4-triethoxysilylbutyl)trisulfide, bis(3-trimethoxysilylpropyl)trisulfide, bis(2-trimethoxysilylethyl)trisulfide, bis(4-trimethoxysilylbutyl)trisulfide, bis(3-triethoxysilylpropyl)disulfide, bis(2-triethoxysilylethyl)disulfide, bis(4-triethoxysilylbutyl)disulfide, bis(3-trimethoxysilylpropyl)disulfide, bis(2-trimethoxysilylethyl)disulfide, bis(4-trimethoxysilylbutyl)disulfide and the like. Among these, bis(3-triethoxysilylpropyl)disulfide is preferable from the viewpoint of processability. These silane coupling agents may be used alone or two or more of these in combination.

The rubber composition preferably further contains a cross-linking agent. Examples of the cross-linking agent include sulfurs, sulfur halides, organic peroxides, quinonedioximes, organic polyvalent amine compounds, and alkylphenol resins having methylol groups. Among these, sulfurs are preferably used. The amount of the cross-linking agent blended is preferably 0.1 to 15 parts by weight, more preferably 0.5 to 5 parts by weight, particularly preferably 1 to 4 parts by weight, with respect to 100 parts by weight of the rubber component in the rubber composition.

In addition to the above-mentioned components, compounding agents such as cross-linking accelerators, cross-linking activators, anti-aging agents, activators, process oils, plasticizers, and lubricants can be added to the rubber composition each in necessary amounts other than the above-described components, according to a conventional method.

When sulfur or a sulfur-containing compound is used as the cross-linking agent, a cross-linking accelerator and a cross-linking activator are preferably used in combination. Examples of the cross-linking accelerator include sulfenamide cross-linking accelerators; guanidine cross-linking accelerators; thiourea cross-linking accelerators; thiazole cross-linking accelerators; thiuram cross-linking accelerator; dithiocarbamate cross-linking accelerators; and xanthogenic acid cross-linking accelerators. Among these, those containing a sulfenamide cross-linking accelerator are preferred. One of these cross-linking accelerators may be used alone or two or more of these in combination. The blending amount of the cross-linking accelerator is preferably 0.1 to 15 parts by weight, more preferably 0.5 to 5 parts by weight, and particularly preferably 1 to 4 parts by weight, based on 100 parts by weight of the rubber component in the rubber composition.

Examples of the cross-linking activator include higher fatty acids such as stearic acid, zinc oxide, and the like. One of these cross-linking activators may be used alone or two or more in combination. The blending amount of the cross-linking activator is preferably 0.05 to 20 parts by weight, particularly preferably 0.5 to 15 parts by weight, based on 100 parts by weight of the rubber component in the rubber composition.

The rubber composition of the present invention may contain a resin other than the rubber component. Blending of the resin imparts tackiness to the rubber composition and improvement in the dispersibility of the filler in the rubber composition. As a result, the obtained cross-linked rubber can be expected to have improvemed wet grip property and abrasion resistance. In addition, as an effect similar to that of the plasticizer, processability of the rubber composition can be improved. Examples of the resin include a C5 petroleum resin, a C5/C9 petroleum resin, a C9 petroleum resin, a dicyclopentadiene resin, a terpene resin, a terpene phenol resin, an aromatic modified terpene resin, an alkylphenol-acetylene resin, a rosin resin, a rosin ester resin, an indene resin, a C9 resin containing indene, an α-methylstyrene/indene copolymer resin, a coumarone-indene resin, a farnesene resin, and a polylimonene resin. These resins may be modified or hydrogenated. One of these resins may be used alone or two or more of these in combination. The blending amount of the resin is preferably 25 parts by weight or less based on 100 parts by weight of the rubber component in the rubber composition.

In order to obtain the rubber composition of the present invention, each of the components may be kneaded in accordance with an ordinary method, and for example, a compounding agent with no thermally unstable component such as a cross-linking agent or a cross-linking accelerator and a rubber component containing a conjugated diene polymer obtained by the production method of the present invention are kneaded, and subsequently a thermally unstable component such as a cross-linking agent or a cross-linking accelerator can be mixed into the kneaded product to obtain a desired composition. The kneading temperature of the compounding agent with no thermally unstable component and the rubber component containing the conjugated diene polymer obtained by the production method of the present invention is preferably 80 to 200° C., more preferably 120 to 180° C., and the kneading time is preferably 30 seconds to 30 minutes. The mixture of the kneaded product and the thermally unstable component is usually cooled to 100° C. or less, preferably 80° C. or less.

<Cross-Linked Rubber>

The cross-linked rubber of the present invention is obtained by cross-linking (vulcanizing) the above-described rubber composition of the present invention. The cross-linked rubber product can be produced by using the rubber composition of the present invention, for example by molding with a molding machine corresponding to a desired shape, for example, an extruder, an injection molding machine, a compressor, a roll, or the like, and heating to carry out a cross-linking reaction and by fixing the shape as a cross-linked product. In this case, cross-linking may be carried out after molding in advance or at the same time as the molding. The molding temperature is usually 10 to 200° C., preferably 25 to 120° C. The cross-linking temperature is usually 100 to 200° C., preferably 130 to 190° C., and the cross-linking time is usually 1 minute to 24 hours, preferably 2 minutes to 12 hours, and particularly preferably 3 minutes to 6 hours.

Further, depending on the shape and size of the cross-linked rubber, the inside of the cross-linked rubber may not be sufficiently cross-linked despite of the surface of the cross-linked rubber being cross-linked, thus further heating may be carried out to perform the second cross-linking.

As the heating method, a general method used for cross-linking a rubber such as press heating, steam heating, oven heating, and hot air heating may be appropriately selected.

Since the cross-linked rubber of the present invention thus obtained is obtained by using the conjugated diene polymer obtained by the production method of the present invention described above, the product is excellent in low heat generation property and wet grip property, and can be suitably used for tires. In particular, making use of such properties, the cross-linked rubber can be used in various applications such as a material for each part of a tire, such as a cap tread, a base tread, a carcass, a sidewall, and a bead part; a material for a hose, a belt, a mat, a vibration-proof rubber, and various other industrial products; an impact resistance modifier for a resin; a resin film buffer; a shoe sole; a rubber shoe; a golf ball; a toy; and the like. In particular, the cross-linked rubber of the present invention can be suitably used in various types of tires such as all-season tires, high-performance tires, and stud-less tires in respective parts of the tire such as a tread, a carcass, a sidewall, and a bead portion, and since the low heat generation property is particularly advantageous, it can be particularly suitably used for a tread of a fuel-efficient tire.

EXAMPLES

In the followings, the present invention will be described in more detail with reference to the Examples; however, the invention shall not be limited to the following Examples as long as the scope of the invention is not exceeded.

<Ethanol Component Evaluation Method>

In the following Examples and Comparative Examples, the contents of Fe and Si in the ethanol were measured using an inductively coupled plasma mass spectrometry (ICP-MS) ELAN DRCII manufactured by Perkin Elmer. The content of the aromatic compounds in the ethanol was measured using a gas chromatography device (GC-2014, manufactured by SHIMADZU).

<1,3-Butadiene Quantitative Method>

Quantitative evaluation of 1,3-butadiene was performed by analysis using a gas chromatography device (GC-2014, manufactured by SHIMADZU). The measurement conditions were as follows.

<Analytical Conditions of GC/MS Method>

Column: Rt-Q-BOND (length 30 m, inner diameter 0.32 mm, film thickness 10 μm)

Oven temperature: 60° C., 11.5 minutes→10° C./min →100° C., 14.5 minutes →10° C./min →250° C.

Sampling time: 5 minutes

Carrier gas: He (30 cm/s)

Split ratio: 75

Reference Example 1

<Preparation of Ethanol>

Ethanol was produced as follows.

(Raw Material Gas Generating Step)

The gas discharged after general waste was combusted in the refuse incinerator was used. The components of the raw material gas were about 30 vol % of carbon monoxide, about 30 vol % of carbon dioxide, about 30 vol % of hydrogen, and about 10 vol % of nitrogen.

(Synthetic Gas Purification Step)

By using a PSA apparatus, which is an impurity removing apparatus, the raw material gas produced as described above was removed of the carbon dioxide contained in the synthetic gas so as to be 60 to 80 vol % of the original content (about 30 vol %) under the condition in which the gas temperature was heated to 80° C., and subsequently, re-cooling was done in a heat exchanger using steam at 150° C. using a double-pipe heat exchanger using the heated gas temperature and cooled water of 25° C. to precipitate the impurities and remove the precipitated impurities with a filter, thereby producing the synthetic gas.

(Microbial Fermentation Step)

The synthetic gas obtained as described above was continuously fed into a continuous fermenter (microbial fermenter) equipped with a main reactor, a synthetic gas supply hole, and a discharge hole and filled with a seed of *Clostridium autoethanogenum* (microorganisms) and a liquid culture medium (containing an appropriate amount of a phosphorus compound, a nitrogen compound, various minerals, and the like) for culturing the microorganisms, and culturing (microbial fermentation) was carried out continuously for 300 hours. Thereafter, about 8000 L of the culture liquid containing the ethanol was withdrawn from the discharge hole.

(Separation Step)

An ethanol-containing liquid was obtained from the culture liquid obtained in the above-described fermentation step using a solid-liquid separation filter device under the condition in which the culture liquid introduction pressure is 200 kPa or more.

(Distillation Step)

Subsequently, the ethanol-containing liquid was introduced into a distillation apparatus equipped with a heater using steam of 170° C. After the temperature at the bottom of the distillation column was raised to 101° C. within 8 to 15 minutes, the ethanol-containing liquid was introduced from the middle of the distillation column, and during continuous operation, the bottom of the column was continuously operated at 101° C., the middle of the column was continuously operated at 99° C., and the top of the column was continuously operated at 91° C. under the condition of 15 seconds/L to obtain purified ethanol. The resulting ethanol contained 0.1 mg/L of iron and 50 mg/L of Si. The resulting ethanol also contained 0.07 mg/L of toluene, 0.8 mg/L of ethylbenzene, and 0.2 mg/L of combined m-xylene and p-xylene.

The content of n-hexane in the obtained ethanol is 0.1 mg/L, n-heptane is 0.04 mg/L, n-octane is 0.02 mg/L, n-decane I is 0.32 mg/L, n-dodecane is 0.1 mg/L, and tetradecane is 0.03 mg/L. The content of dibutyl ether in the obtained ethanol was 20 mg/L.

(Method for Producing 1,3-Butadiene)

1,3-butadiene was produced using the ethanol obtained as described above. First, the obtained ethanol was vaporized by passing ethanol through a single pipe heated to 90° C. to form a gas to be used for the reaction, and the vaporized ethanol gas was combined with nitrogen. At this time, the flow rate of the ethanol gas was controlled by a mass flow so as to be SV360 L/hr/L and the nitrogen gas to be SV840 L/hr/L, thereby obtaining a mixed gas of 30 vol % of ethanol (converted to gas) and 70 vol % of nitrogen (converted to gas). Subsequently, by continuously supplying the above-mentioned mixed gas to a cylindrical stainless steel reaction tube having a diameter of ½ inches (1.27 cm) and a length of 15.7 inches (40 cm), which was filled with 0.85 g of a catalyst for 1,3-butadiene synthesis mainly composed of Hf and Zn, while maintaining a temperature of 325° C. and a pressure (pressure of the reaction bed) of 0.1 MPa, 1,3-butadiene-containing gas was obtained. The content of 1,3-butadiene in the obtained 1,3-butadiene-containing gas was quantified using a gas chromatography apparatus of GC-2014 (manufactured by SHIMADZU). The results are shown in Table 1.

Reference Comparative Example 1

Using 99 degrees ethanol (manufactured by Amakasu Chemical Industries), which is ethanol derived from fossil fuels, 1,3-butadiene was produced in the same manner as in Reference Example 1, and the content of 1,3-butadiene was quantified in the same manner as in Reference Example 1. The results are as shown in Table 1. The content of iron in the 99 degrees ethanol, the fossil-fuel-derived ethanol, was 2.8 mg/L, and the content of Si was unmeasurable (below the detection limit, less than 10 mg/L). The content of toluene in the ethanol obtained was unmeasurable (below the detection limit, less than 0.01 mg/L), the content of ethylbenzene was not measurable (below the detection limit, less than 0.1 mg/L), and the total content of m-xylene and p-xylene was unmeasurable (below the detection limit, less than 0.2 mg/L).

Reference Comparative Example 2

Using 99 degrees ethanol (manufactured by Amakasu Chemical Industries) derived from saccharization and fermentation of plants, 1,3-butadiene was produced in the same manner as in Reference Example 1, and the content of 1,3-butadiene was quantified in the same manner as in Reference Example 1. The results are as shown in Table 1. The iron content in 99 degrees ethanol derived from plant saccharization and fermentation was below the detection limit (less than 0.0001 mg/L), and the Si content was unmeasurable (less than the detection limit, less than 10 mg/L). The content of toluene in the ethanol obtained was unmeasurable (below the detection limit, less than 0.01 mg/L), the content of ethylbenzene was unmeasurable (below the detection limit, less than 0.1 mg/L), and the total content of m-xylene and p-xylene was unmeasurable (below the detection limit, less than 0.2 mg/L).

TABLE 1

| | | Ethanol | | | | |
| --- | --- | --- | --- | --- | --- | --- |
| | Type | Fe Content (mg/L) | Si Content (mg/L) | Total Content of Aromatic Compounds (mg/L) | 1,3-butadiene content (vol %) | 1,3-butadiene purity (vol %) |
| Reference Example 1 | Derived from Synthetic Gas | 0.1 | 50 | 1.07 | 61.2 | 84.5 |
| Reference Comparative Example 1 | Derived from Fossil Fuel | 2.8 | Less than 10 | Less than 0.31 | 57.2 | 80.2 |
| Reference Comparative Example 2 | Derived from Saccharization and Fermentation | Less than 0.0001 | Less than 10 | Less than 0.31 | 57.5 | 81.6 |

As shown in Table 1, it was found that the ethanol produced using the gas discharged after combustion of general waste in a refuse incinerator had higher conversion efficiency to 1,3-butadiene than that of the ethanol derived from the conventional fossil fuels or the ethanol derived from saccharization and fermentation of plants.

(Evaluation Method for SBR)

The styrene-butadiene rubber (SBR) synthesized below was evaluated by the following method.

Average molecular weight and dispersion degree

The number-average molecular weight (Mn) and the weight-average molecular weight (Mw) were calculated from GPC measurement using a column of Shodex GPC KF-806 L (manufactured by Showa Denko K.K.) in HLC-8420GPC (manufactured by Tosoh). Using THF as an eluent and polystyrene as a standard substance, a solution having a sample concentration of 0.2 w/v % was prepared. 100 μL of the prepared sample was injected at a flow rate of 1.0 mL/min. The column temperature was 40° C. The dispersion degree was determined as Mw/Mn.

Glass transition temperature (Tg)

Using a thermal analyzer EXSTAR DSC7020 (manufactured by Hitachi High-Tech Science Co., Ltd.), the glass transition temperatures were measured in a temperature range of −100° C. to 100° C., a temperature elevation rate of 20° C./min.

Example 1

(Synthesis of SBR)

The 1,3-butadiene (iron content in the raw material ethanol: 0.1 mg/L) produced in Reference Example 1 was cooled to 10 degrees still in the form of gas and subjected to gas-liquid separation to obtain purified butadiene. At this time, the purity of butadiene was 70%, butadiene/oxygen-containing compound =3.6, and butadiene/hydrocarbon compound=6.2. After 129 g of water was added to a 1 L pressure resistant reaction vessel, 3 L of nitrogen gas was bubbled (about 50 mL/min×1 hour). Next, 11.6 g of a 25% aqueous solution of potassium rosinate, 0.097 g of potassium oleate, 0.52 g of sodium phosphate, 0.097 g of Rongalite, 0.13 g of paramenthane hydroperoxide, and 16.2 g of styrene were added. The reaction vessel was immersed in a water bath cooled to 5° C., and 48.4 g of purified butadiene was charged while stirring. Thereafter, 0.032 g of ferric sulfate and 0.045 g of EDTA-4Na were added as initiators. After 20 hours, 0.13 g of N, N'-dimethyldithiocarbamate was added to stop the reaction, and latex (styrene-butadiene rubber) was obtained.

To the resulting latex was added a few drops of sulfuric acid and the product was stirred in water. The water was filtered, then washing with water was conducted until the washing liquid became neutral, and the product was then dissolved in THF. The solvent was washed with methanol and then dried under reduced pressure to obtain a solid rubber (emulsion polymerization SBR). The yield was 44%. Upon analysis, the Mn of the obtained polymer was 91,800, Mw was 492,000, and Mw/Mn was 5.36. The glass transition temperature was −46.5° C.

Comparative Example 1

A solid rubber (emulsion polymerization SBR) was obtained in the same manner as in Example 1, except that 1,3-butadiene (iron content in the raw material ethanol: less than 2.8 mg/L) produced in Reference Comparative Example 1 was used as 1,3-butadiene. The yield was 29%. Upon analysis, the Mn of the obtained polymer was 82,400, Mw was 382,000, and Mw/Mn was 4.64. The glass transition temperature was −40.3° C.

Comparative Example 2

A solid rubber (emulsion polymerized SBR) was obtained in the same manner as in Example 4, except that 1,3-butadiene (iron content in the raw material ethanol: equal to or less than the detection limit (less than 0.0001 mg/L)) prepared in Reference Comparative Example 2 was used as 1,3-butadiene. The yield was 43%. Upon analysis, the Mn of the obtained polymer was 67,200, Mw was 297,000, and Mw/Mn was 4.42. The glass transition temperature was −47.1° C.

(Iron-Containing Effect)

When the iron content of the ethanol is in the range of 0.0001 to 2 mg/L, it can be understood from the Examples and Comparative Examples that Mw/Mn falls within the range of 4.7 to 6.0. When iron is present in the ethanol in the range of 0.0001 to 2 mg/L, trace oxygen mixed in can be adsorbed, and generates a side reaction at the time of butadiene synthesis which interfere the ongoing polymerization reaction, thereby improving the selectivity of butadiene. By using a high-purity butadiene, the ratio of styrene to butadiene can be precisely controlled, and Mw/Mn can be kept within the range of 4.7 to 6.0. The presence of iron in the ethanol at 2 mg/L or more increases the amount of butane in the butadiene gas formed during the butadiene synthesis reaction. It is considered that the presence of butane, which does not act on the polymerization reaction during the emulsion polymerization, lowers the proportion of butadiene in the polymer and increases the value of Mw/Mn.

When the iron content of the ethanol is in the range of 0.0001 to 2 mg/L, it can be understood from the Examples and Comparative Examples that the polymerization yield improves. It is considered that if iron is present in the ethanol in the range of 0.0001 to 2 mg/L, trace oxygen mixed in can be adsorbed, and deactivation of the catalyst due to oxygen during emulsion polymerization can be prevented, resulting in a high polymerization yield. On the other hand, if the ethanol contains 2 mg/L or more of iron, the amount of butane mixed into the butadiene gas produced in the course of the butadiene synthesis reaction increases. It is considered that the presence of butane which does not act on the polymerization reaction in the emulsion polymerization lowers the proportion of butadiene in the polymer and lowers the polymerization yield.

When the iron content of the ethanol is in the range of 0.0001 to 2 mg/L, it can be understood from the Examples and Comparative Examples that the glass transition temperature falls within the range of −41 to −47° C. The presence of iron in the ethanol increases the amount of ethyl acetate mixed into the butadiene gas produced in the course of the butadiene synthesis reaction. It is considered that the presence of ethyl acetate in the emulsion polymerization lowers the crystallinity of the molecules and lowers the glass transition temperature by partially incorporating ethyl acetate into the inside of the rubber. On the other hand, if the ethanol contains 2 mg/L or more of iron, it is considered that the amount of ethyl acetate mixed in the butadiene gas generated in the course of the butadiene synthesis reaction increases too much and the glass transition temperature becomes too high.

The invention claimed is:

1. A method for producing a non-petrochemical-derived conjugated diene polymer using an alcohol derived from a non-petrochemical raw material, comprising the steps of:
   using an alcohol having an iron content of 0.0001 mg/L to 2 mg/L derived from a non-petrochemical raw material, bringing the alcohol into contact with a catalyst and carrying out heating to produce a conjugated diene having $C_4$ to $C_{12}$ carbons; and
   polymerizing a monomer containing the conjugated diene to produce a non-petrochemical derived conjugated diene polymer.

2. The method according to claim 1, wherein the alcohol derived from a non-petrochemical raw material comprises ethanol.

3. The method according to claim 1, wherein the conjugated diene comprises at least one selected from the group consisting of 1,3-butadiene, isoprene, 1,3-pentadiene, 2,3-dimethyl-1,3-butadiene, 2-methyl-1,3-pentadiene, 1,3-hexadiene, 4,5-diethyl-1,3-octadiene, and 3-butyl-1,3-octadiene.

4. The method according to claim 1, wherein the alcohol derived from a non-petrochemical raw material is produced by using a gas containing carbon monoxide and hydrogen as a substrate.

5. The method according to claim 1, wherein the alcohol derived from a non-petrochemical raw material is derived from microbial fermentation.

6. The method according to claim 4, wherein the gas comprising carbon monoxide and hydrogen is derived from waste.

7. The method according to claim 1, wherein an aromatic hydrocarbon is further polymerized as a monomer.

8. The method according to claim 7, wherein the aromatic hydrocarbon is at least one selected from the group consisting of styrene, methylstyrene, ethylstyrene, t-butylstyrene, α-methylstyrene, α-methyl-p-methylstyrene, chlorostyrene, bromostyrene, methoxystyrene, dimethylaminomethylstyrene, dimethylaminoethylstyrene, diethylaminomethylstyrene, diethylaminoethylstyrene, cyanoethylstyrene, and vinylnaphthalene.

9. The method according to claim 1, wherein the conjugated diene polymer includes at least one selected from the group consisting of isoprene rubber, butadiene rubber, styrene butadiene rubber, chloroprene rubber, and acrylonitrile butadiene rubber.

10. A method for producing a cross-linked rubber, comprising the step of kneading the non-petrochemical-derived conjugated diene polymer obtained as a rubber component by the method according to claim 1 with a filler, and carrying out cross-linking.

* * * * *